(12) United States Patent
Patel

(10) Patent No.: US 9,498,302 B1
(45) Date of Patent: Nov. 22, 2016

(54) MAGNETIC ORTHODONTIC ASSEMBLY

(71) Applicant: Ruchir Ramesh Patel, Alpharetta, GA (US)

(72) Inventor: Ruchir Ramesh Patel, Alpharetta, GA (US)

( * ) Notice: Subject to any disclaimer, the term of this patent is extended or adjusted under 35 U.S.C. 154(b) by 0 days.

(21) Appl. No.: 14/696,625

(22) Filed: Apr. 27, 2015

Related U.S. Application Data

(63) Continuation-in-part of application No. 14/262,843, filed on Apr. 28, 2014, now abandoned.

(60) Provisional application No. 62/064,218, filed on Oct. 15, 2014.

(51) Int. Cl.
*A61C 7/00* (2006.01)
*A61C 7/08* (2006.01)

(52) U.S. Cl.
CPC ........ *A61C 7/006* (2013.01); *A61C 7/08* (2013.01)

(58) Field of Classification Search
CPC .......... A61C 7/14; A61C 7/148; A61C 7/12; A61C 7/006; A61C 7/08
USPC ................................ 433/8, 10, 16, 17, 24, 6
See application file for complete search history.

(56) References Cited

U.S. PATENT DOCUMENTS

| | | | |
|---|---|---|---|
| 3,984,915 A | 10/1976 | Noble | |
| 4,484,895 A | 11/1984 | Smiley et al. | |
| 4,496,317 A * | 1/1985 | Hulsey | A61C 7/12 433/10 |
| 5,238,404 A * | 8/1993 | Andreiko | A61C 7/12 433/20 |
| 5,466,151 A | 11/1995 | Damon | |
| 5,618,175 A * | 4/1997 | Reher | A61C 7/141 433/16 |
| 5,975,893 A | 11/1999 | Chisti et al. | |
| 6,866,505 B2 * | 3/2005 | Senini | A61C 7/287 433/10 |
| 7,168,950 B2 * | 1/2007 | Cinader, Jr. | A61C 7/146 433/2 |
| 7,431,586 B1 * | 10/2008 | Silverman | A61C 7/14 433/9 |
| 7,704,072 B2 * | 4/2010 | Damon | A61C 7/287 433/11 |
| 7,819,661 B2 | 10/2010 | Nadav | |
| 8,356,993 B1 | 1/2013 | Marston | |
| 8,439,671 B2 * | 5/2013 | Cinader, Jr. | A61C 19/004 433/24 |
| 8,465,279 B2 * | 6/2013 | Bathen | A61C 7/28 433/16 |
| 2008/0293005 A1 * | 11/2008 | Rahlis | A61C 7/02 433/16 |
| 2010/0075269 A1 * | 3/2010 | Mutschler | A61C 7/08 433/10 |
| 2010/0183997 A1 | 7/2010 | Darendeliler | |
| 2011/0311935 A1 * | 12/2011 | Dumas | A61C 7/14 433/16 |
| 2015/0086936 A1 * | 3/2015 | Owen | A61C 7/00 433/10 |

* cited by examiner

*Primary Examiner* — Nicholas Lucchesi
(74) *Attorney, Agent, or Firm* — The Law Offices of Konrad Shavinian; Thomas Paulius

(57) ABSTRACT

An orthodontic assembly for moving selected teeth of a patient includes a hollow aligner shell that fits over a set of selected teeth. The aligner shell supports a series of tooth moving elements, such as magnets or metal engagement plates that are fixed in place in alignment with the selected teeth. Metal plates or magnets are affixed to the selected teeth and when the aligner shell is fitted over the teeth, the magnets in the shell exert attraction or repulsion forces on the metal plates to move the selected teeth in accordance with a treatment protocol.

17 Claims, 15 Drawing Sheets

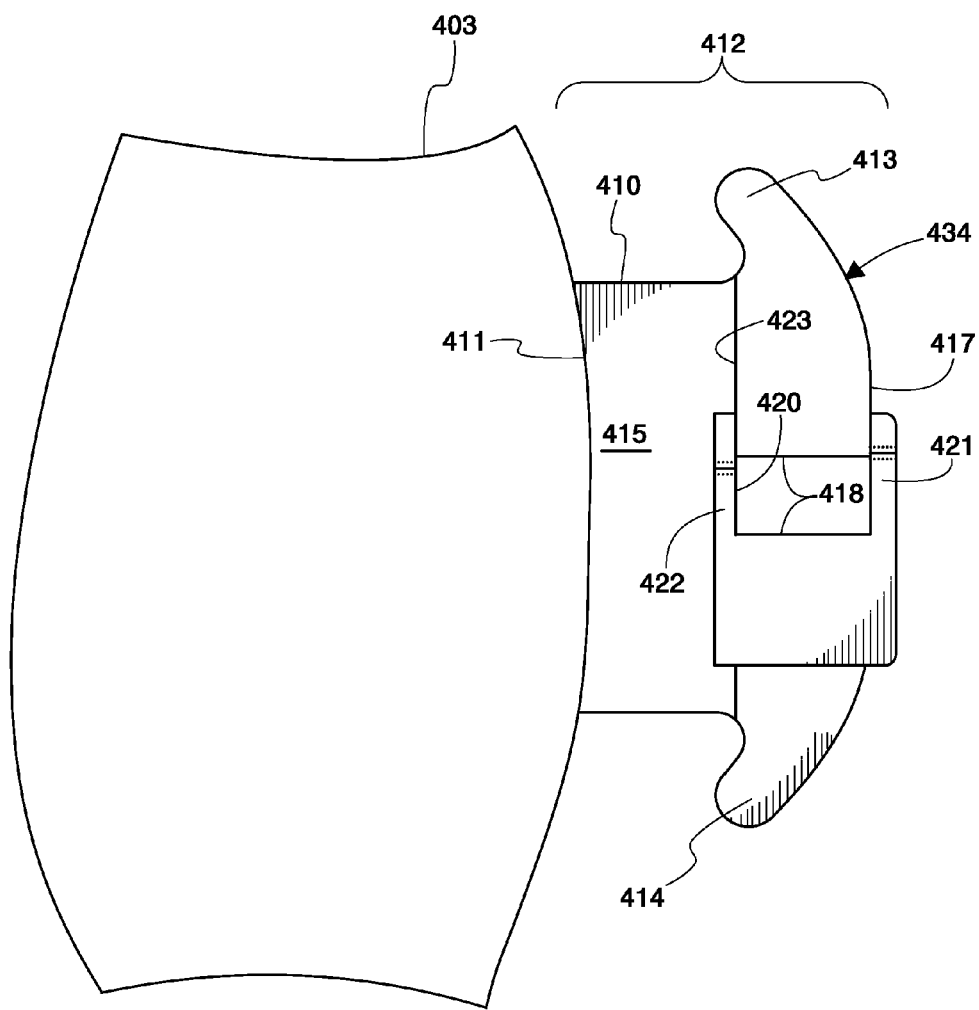

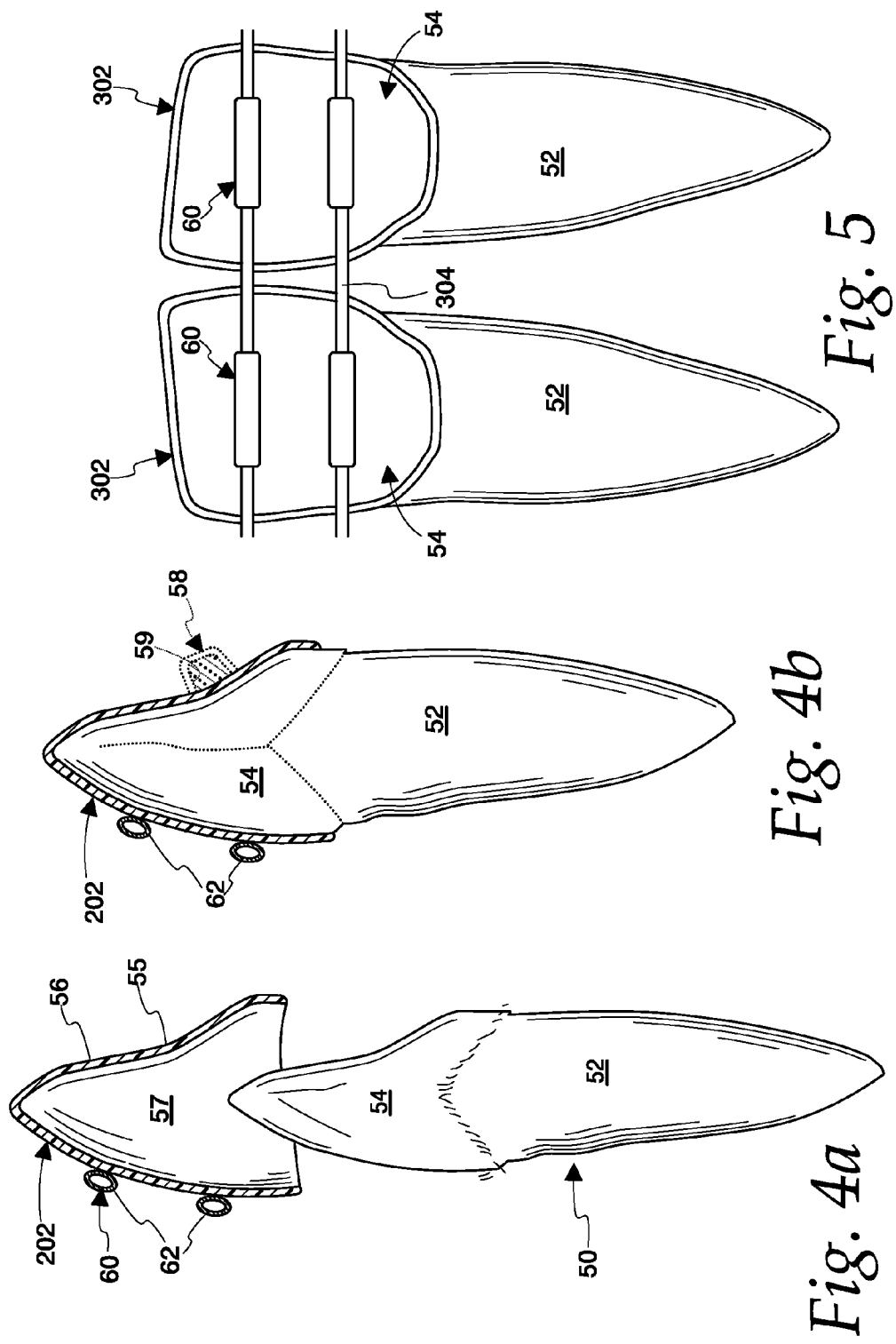

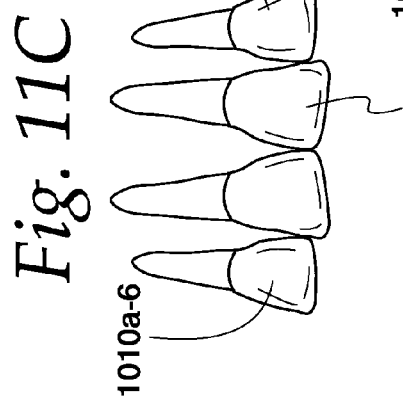
Fig. 11C
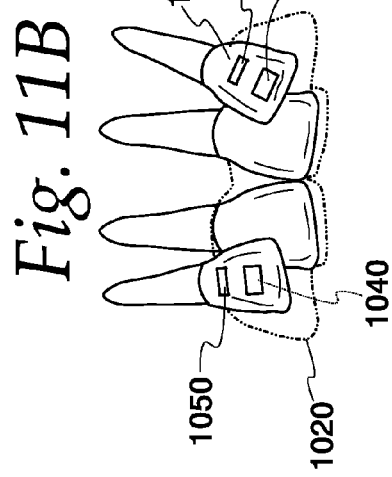
Fig. 11B
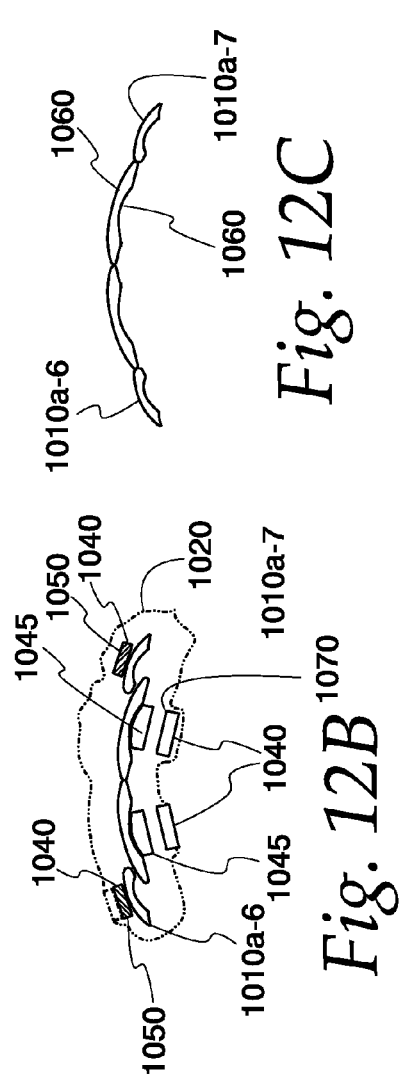
Fig. 12C
Fig. 12B
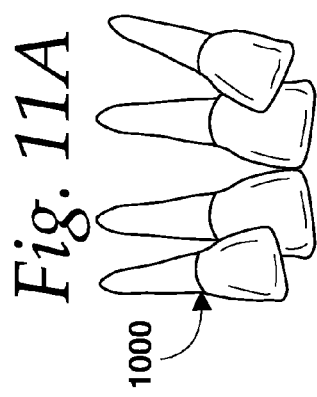
Fig. 11A
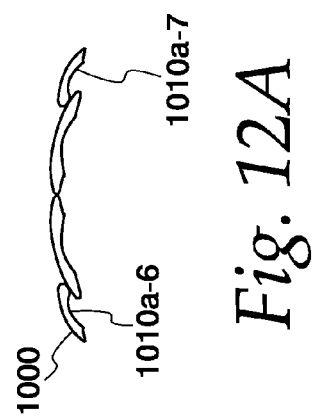
Fig. 12A

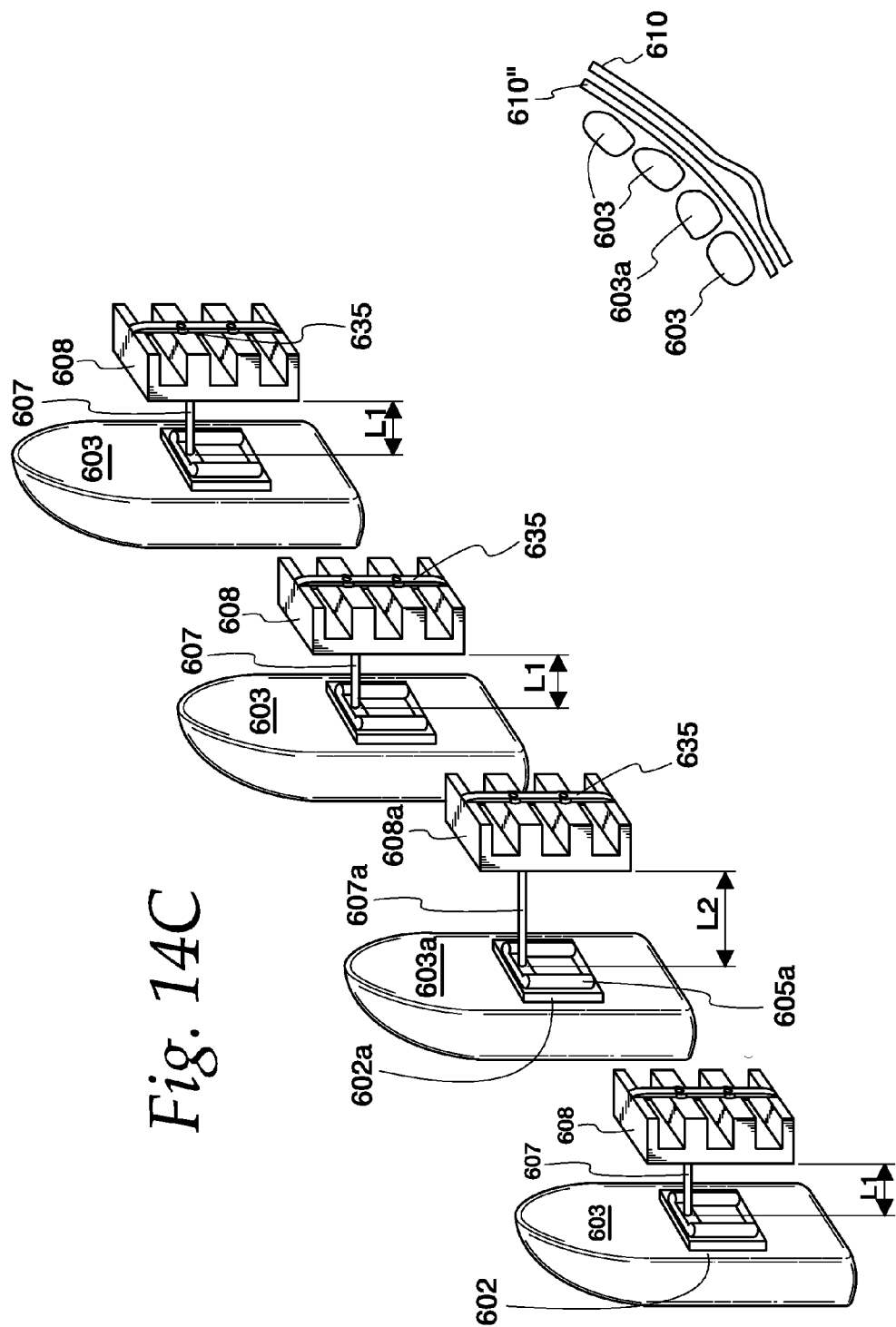

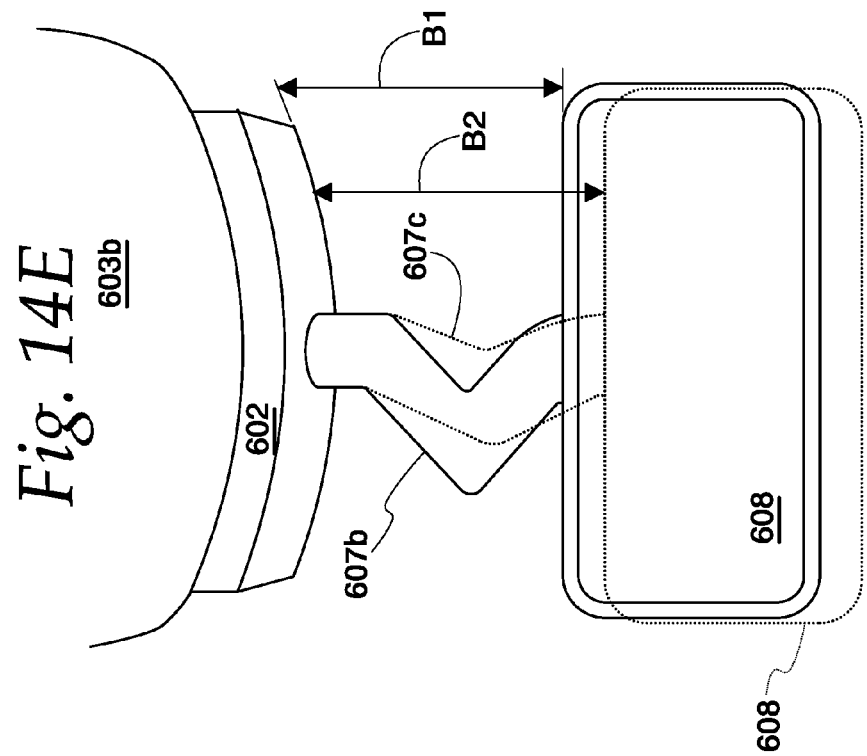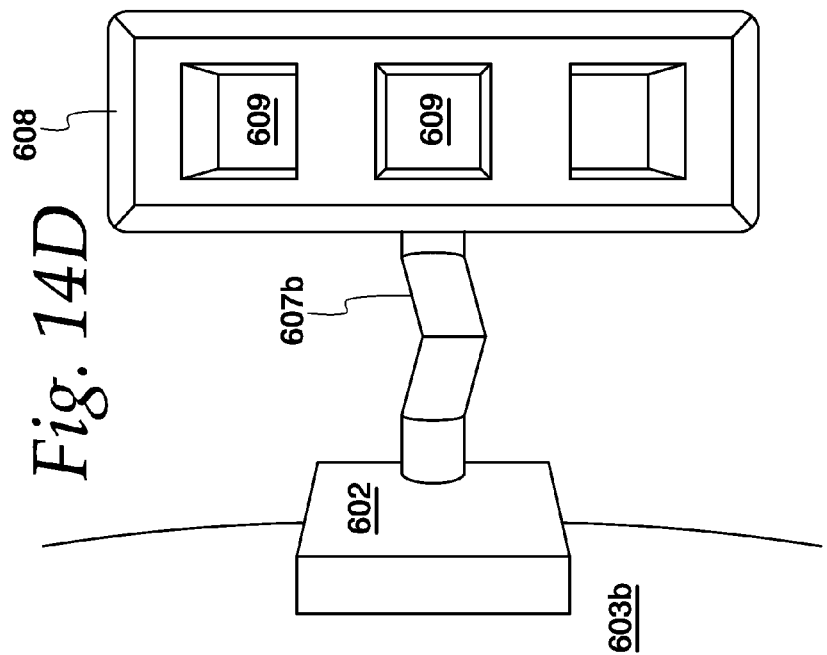

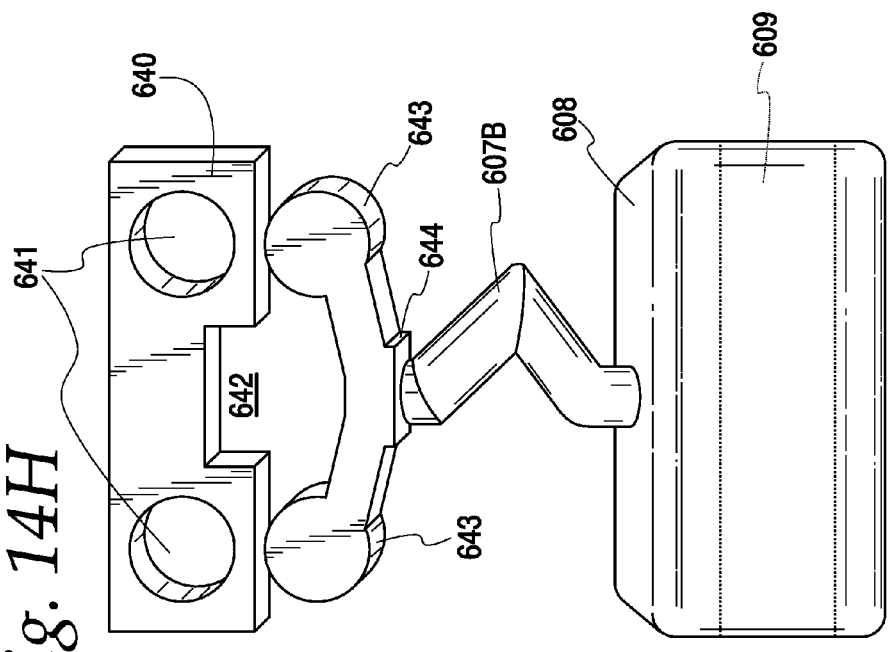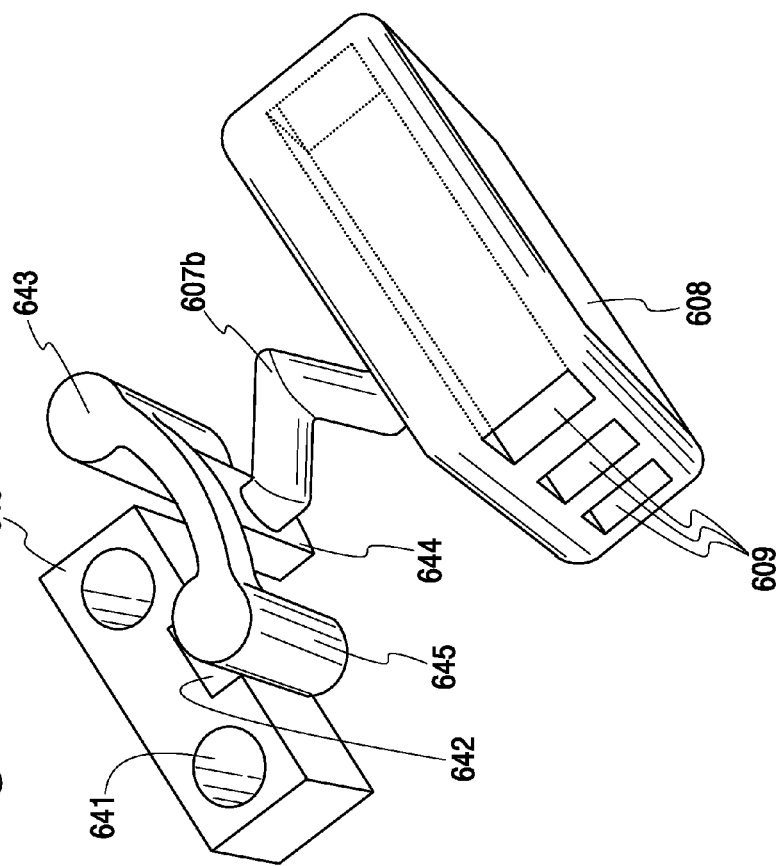

MAGNETIC ORTHODONTIC ASSEMBLY

REFERENCE TO RELATED APPLICATIONS

This application is a continuation-in-part application of prior U.S. non-provisional patent application Ser. No. 14/262,843, filed Apr. 28, 2014 and entitled "System For Moving and Aligning Teeth." I hereby claim priority to said Ser. No. 14/262,843 under 35 U.S.C. §120. I also claim priority to prior U.S. provisional patent application Ser. No. 62/064,218, filed Oct. 15, 2014 for "Magnetic Orthodontic Appliance."

BACKGROUND OF THE DISCLOSURE

The present disclosure relates generally orthodontic devices and assemblies. More particularly, the present disclosure relates to an assembly applied to a patient's teeth or repositioning the patient's teeth through the application of modest force on out-of-position, or out of occlusion teeth so that the out-of-position teeth are moved from their initial position to a final position.

Repositioning teeth for aesthetic or other functional or hygiene purposes is generally accomplished through the use of various orthodontic devices and assemblies which are typically termed "appliances" in the art. Traditional braces are still widely used and include a variety of components, such as brackets, archwires, ligatures, elastics bands and O-rings. Attaching the components to a patient's teeth is a time-consuming and tedious process requiring multiple sessions between a patient and orthodontist. The use of fixed oral appliances also mean that more diligent brushing and flossing is needed for proper dental hygiene. Higher discomfort levels than aligner or removable appliance and restriction of certain kind of foods is also a negative for fixed orthodontic treatment, such as braces. Given the numerous meetings between patient and orthodontist, discomfort to the wearer, and some emergencies with poking wire or broken brackets, the experience of orthodontic treatment with braces can be unpleasant.

Before bonding braces to a patient's teeth, an orthodontist will take x-rays, perform a clinical exam and evaluation, and subsequently take photographs and the like of the patient's teeth and possibly jaw structure. A mold of the patient's teeth may also be made, or a digital impression may be captured on a computer via a digital scanner, so that the orthodontist can use it in conjunction with the x-rays to formulate a treatment strategy. The orthodontist then schedules multiple meetings with the patient to put attach the fixed orthodontic components onto the patient's teeth and assemble them in an initial position.

At the initial brace bonding appointment, brackets and other holding components may be bonded to the patient's teeth. This is accomplished by first by a simple prophylaxis followed by treating the exterior surfaces of selected teeth with a weak acid in order to optimize the adhesion properties of the teeth surfaces for the brackets and bands that are to be bonded to them. The brackets and bands are then cemented to the patient's teeth using a suitable bonding dental material which holds the appliance components in place through the course of treatment.

Generally, an archwire, which can be constructed of a nickel titanium (nitinol) alloy is used to provide a straightening force on the patient's teeth during the initial phases of treatment. The archwire shape and size progression from nitinol to stainless steel is at the discretion of the treating orthodontist The archwire is passed through the brackets over the patient's teeth. It is sized to stretch over the patient's non-straight teeth and when tightened, the archwire exerts a force on the selected teeth to incrementally move them in alignment with other teeth and in accordance with the plan of treatment. As the selected teeth move toward their proper alignment, slack develops in the archwire. As slack develops the ends of the archwire can extend past the last bracket, or tube, installed on the patient's teeth, and the free end(s) of the archwire can cause cuts or discomfort. Accordingly, as the patient's teeth straighten, additional visits to the orthodontist are required to adjust the archwire. In some instances, the visit has an emergency nature that is required to alleviate the patient's discomfort. In addition, braces using exterior brackets also tend to interfere with a patient's ability to brush, floss, and perform other dental hygiene.

There are aligner-based system currently in use which accomplish tooth movement using multiple plastic aligners. One such system is known in the trade as the "Invisalign System". This system uses a series of sets of individual, removable plastic trays (called aligners), each of which is designed to exert a slight force on a selected set of a patient's teeth to move then from an initial mal occlusion and non-ideal configuration toward a final straightened and desired orthodontic configuration. These aligners are changed usually every 2 weeks, or at an interval recommended by the orthodontist. The advantage to these type of systems lies in the removable nature of the aligners, as oral hygiene is easy to maintain and there are no food restrictions. The aligners are also clear and less noticeable and more comfortable as the teeth movement forces are not as severe as braces. Almost no emergency situations arise as patients can remove these from their mouth during eating, at any social event, etc. As the alignment movement progresses, different aligners are used with the patient. The Invisalign and other aligner-based treatment often takes longer than the traditional fixed wire brace system to correct initial crowding or rotations of teeth if crowding and rotations are moderate to severe.

Other disadvantages of aligner-based systems occur in that the patient's teeth (mostly the lateral incisors in the upper arch and the lower incisors) lose tracking of the aligners due to their shape and size, and new impressions or digital dental scans are needed during mid treatment if patient's aligners are not fitting well. It is also hard to extrude teeth; i.e., to bring teeth toward the biting surface from the gum surface using such a system, as no wires attached to selected teeth are utilized and hence, it is difficult to develop an ideal extrusion force on a selected tooth. In fact, aligner systems accomplish their goals, but it takes an extensive time period and a number of trays to extrude teeth, correct rotations and resolve tooth crowding that is moderate to severe. Consequently, it is not uncommon for orthodontists to use fixed braces initially or during the certain phase of orthodontic treatment for 3-6 months or more of orthodontic treatment to establish final occlusion due to the same reasons.

The present disclosure is therefore directed to a less complicated and more efficient orthodontic system including assemblies that minimize patient discomfort and which are more easily installed in a patient.

SUMMARY OF THE PRESENT DISCLOSURE

Accordingly, there is provided an improved orthodontic assembly that is suitable for aligning teeth with minimal attachment to the patient.

An improved system for aligning, or repositioning teeth from an initial, mal-alignment to a final desired alignment is disclosed. In one embodiment in accordance with the principles of the present disclosure, the system comprises a plurality of trays that are utilized in the back of the patient's mouth and which are configured to apply a desired straightening force to a patient's upper and lower back teeth. A set of caps, or covers, are also provided and these tooth caps preferably are configured to fit over selected individual teeth of a patient. The tooth caps are joined together by an archwire to the trays. The archwire is adapted to provide a straightening force on the patient's front teeth, over which the tooth caps are configured to fit. Each tooth cap incorporates a guide on an outer surface thereof through which the archwire can pass. A pair of distalmost brackets, or tubes, are disposed on the left and right trays, and the archwire terminates at the distalmost brackets. This allows a patient to remove the entire orthodontic appliance in one action, to thereby utilize standard hygiene practices for his or her teeth.

In further developed embodiments of the disclosed system, the system includes a lower left tray, a lower right tray, and an upper left tray, and an upper right tray. The trays can be constructed of an elastomeric polymeric shell. In addition, the tooth caps, which are adapted to be placed on a patient's teeth that need movement as determined by an orthodontist, can also be constructed of an elastomeric polymeric shell. Further, the archwire can be constructed of a nickel titanium alloy, such as nitonol. In addition, the wire guide disposed on each cap can be 1) a metal bracket having a center cavity and a movable front gate or 2) a tube which can hold the wire.

As described in this first embodiment, two of the tooth trays are interconnected together with one or more tooth caps. The tooth caps are preferably formed to fit individual teeth but may be formed so that they fit over and engage multiple teeth. The archwires are attached to the trays and the tooth caps and not to the teeth themselves. In this manner, the appliance may be removed by the patient. The archwires are secured to the trays and tooth caps by adhering brackets, or other supports that engage the trays and/or tooth caps by way of adhesion or other suitable means of fixing. Theses supports may take the form of brackets, or they can take the form of hollow tubes through which the archwire passes or other suitable support. When the archwire is tightened, it exerts a force on the selected tooth cap(s) and movement of the selected tooth/teeth is effected over time.

In another embodiment of the present disclosure metal pads or engagement plates may be affixed to the buccal or lingual surface of teeth at selected locations. The archwire extends through brackets, tubes or other support members, and these support members are magnetized with a sufficient magnetic force so that they reliably engage the pads or engagement plates in a fashion to exert tooth moving forces thereupon. The magnetic force is also preferably sufficient such that the support members do not lose contact with the pads or plates during normal operation of the mouth of the patient. Thus, the archwire and its associated support members may be removed by the patient for flossing and other hygiene, or for meals and attendance at social events by disengaging them from the pads or plates and later re-engaging them.

In yet another embodiment, no magnets are used, but instead base plates, or pads, are affixed to the selected teeth in accordance with the course of treatment selected by the orthodontist. Wire guides, or brackets are spaced-apart from the base pads or plates, preferably by way of posts. These posts are of varying lengths in accordance with the manner of treatment, so that an orthodontist may eliminate the need for stepping in the archwire in or out to align teeth. The brackets or wire guides may also include a plurality of slots formed therein so that forming stepping up or stepping down bends in the archwire can be eliminated. Instead, the archwires can be simply and easily passed through appropriate slots in the brackets to exert specific forces on the selected teeth and eliminate the need for wire bending that is presently accomplished with rigid stainless steel archwires that cause sporadic discomfort to the patient. Instead, the archwire may be made of a flexible wire such as nitinol wire and the orthodontist need only choose a bracket with a longer or shorter post in order to maintain the archwire in the desired orientation along the outside surface of the patient's teeth. The archwire support brackets may be provided with a plurality of wire-receiving slots, or tubes, so that a shape-memory alloy archwire, such as one made from nitinol, may be positioned in various slots so that the difference in elevations will accommodate the archwire in an unstepped curve along the front surfaces of the teeth and thereby eliminate the need for stepping the archwire either up or down. In this manner, the shape-memory will be activated in the patient's mouth and seek to return to its original shape and thereby exert a tooth-moving force on the bracket and on the corresponding tooth. The plurality of wire-receiving slots permits the forces to be applied to selected teeth in an incremental manner. In addition, the posts that connect the brackets to the teeth may be formed with a bend in them that permits the orthodontist to adjust the length of the post by increasing or decreasing the bracket to tooth distance by manipulating the post with a pliers.

Accordingly, systems of the present disclosure will enable an orthodontist to monitor and conclude orthodontic treatment without bending rigid wires and consequently use nickel-titanium (nitinol) wires in place of stainless steel wires throughout orthodontic treatment. Nitinol archwires are more comfortable for patients as the tooth movement forces generated thereby maintain a low but constant level of movement force. Many orthodontic bracket systems contain hooks for wearing elastics in mouth to align bite and occlusion. Such hooks will be placed on pads in this system as needed.

In another embodiment according to the present disclosure, one or more aligner trays, or shells, are provided. The aligners include impressions of the patient's teeth and may be formed with extra room to accommodate the movement of the selected teeth as well as room for tooth moving elements, such as metal plates or magnets. These tooth moving elements are affixed to either the lingual or buccal tooth surfaces based on the orthodontist's preference. The pads/plates/magnets will attract or repel the magnets or vice-versa creating a strategic tooth moving force system. The magnets may be disposed on the aligner trays and couple with corresponding metal plates attached to selected teeth in order to provide tooth moving forces. Conversely, the metal plates may be affixed to the aligner trays while the magnets are affixed to the selected teeth to form coupled pairs of tooth moving elements. The magnets and metal plates may be associated in manners other than simple pairs to provide special movement forces on selected teeth, such as two magnets of opposite polarity may be affixed to the aligner and teeth in order to exert a magnetic repulsion force on the teeth in specific directions. The magnets and metal plates may also be mixed in arrangements so that the aligner shell and teeth each include magnets and metal plates. A metal plate may also be used on another tooth surface in opposition to a magnet supported by the aligner to exert an additional movement force on the selected tooth in addition to the aforementioned repulsion forces. In either instance, the aligner trays are removable by the patient so that proper hygiene may be maintained, or the aligner trays removed for attendance at social events, all of which facilitate and ease the orthodontic experience. Additionally, the aligner tray structures may be easily made in an out-of-mouth environment to accommodate multiple, different arrangements of the magnets and metal plates and the length of the aligners may run from the full length of the teeth to smaller lengths that accommodate fewer teeth.

In this manner, the aligners apply tooth movement forces to selected teeth without the need for archwires. The magnets preferably have magnetic forces of between about 50 grams and about 400 grams of force, which may exert constant, stronger and more controlled tooth movement forces than those exerted by ordinary aligner systems. The coupling of stronger tooth movement forces and the ability to remove the aligners for hygiene, dining and other similar occurrences provide greater comfort benefits to patients.

Accordingly, it is an object of the present disclosure to provide an improved system for moving teeth from an initial unstraightened configuration to a final straightened configuration.

Another object of the present disclosure is to provide a system for moving teeth that minimizes patient meetings with an orthodontist.

Yet another object of the present disclosure is to provide a system for moving teeth that eliminates emergency patient meetings with an orthodontist.

Still another object of the present disclosure is to provide a system for moving teeth that allows a patient to utilize standard dental hygiene.

A still further object of the disclosed system is to provide a fully removable system for moving teeth in a preselected arrangement.

Yet still a further object of the present disclosure is to provide an orthodontic assembly in which one or more tooth caps are interconnected together to at least two trays by way of at least one archwire that extends over the front surfaces of the tooth caps and trays and in which the tooth caps and trays include metal anchor pads and the archwire includes magnetized supports that magnetically engage the anchor pads to thereby hold the tooth caps and trays in a preselected orientation.

And yet another object of the present disclosure is to provide an orthodontic appliance for moving teeth in a patient's mouth in which one or more aligner trays are provided that cover a series of selected teeth, the aligner trays supporting a plurality of tooth moving elements thereon, such as magnets or metal plates, while the teeth support a plurality of corresponding opposing tooth moving elements such as magnets or metal plates to form magnetically coupled pairs of tooth moving elements that exerting movement forces on selected teeth of the patient, and the aligner trays being removable and insertable by the patient.

Another object of the present disclosure is to provide a system for moving teeth that utilizes flexible archwires in association with multi-slotted wire guide brackets that are mounted on selected teeth with posts, the posts being of different lengths so as to apply preselected tooth moving forces on preselected teeth.

Another object of the present disclosure is to provide a bracket system for moving teeth that utilizes flexible archwires in association with multiple vertical slots connected with the pad (that bonds to tooth surface) by a bendable metal rod welded or connected between the pad and bracket.

These and other objects, features and advantages of the present disclosure will be clearly understood through a consideration of the following detailed description.

BRIEF DESCRIPTION OF THE DRAWINGS

The organization and manner of the structure and operation of the disclosure, together with further objects and advantages thereof, may best be understood by reference to the following detailed description, taken in connection with the accompanying Figures, wherein like reference numerals identify like elements, and in which:

FIG. 3 is a side elevational view of a tooth illustrating a support bracket mounted on its front surface;

FIG. 4A is a side view of a tooth cap in accordance with the present disclosure in position to fit over a tooth;

FIG. 4B is the same view as FIG. 4A, but with the tooth cap in place on its corresponding tooth and with an alternate means of securing the tooth cap to the cap illustrated;

FIG. 5 is a front elevational view of a pair of adjacent teeth with tooth caps in place thereon and with supports in the form of tubes affixed thereto;

FIG. 11A is a front elevational view of four incisors of a patient in need of alignment;

FIG. 11B is the same view as FIG. 11A, but with metal plates affixed to the teeth and the teeth enveloped by an aligner for those four teeth, with magnets oriented with the metal plates for selected movement of the teeth;

FIG. 11C is the same view as FIG. 11B, showing the teeth aligned together after movement and removal of the aligner and metal plates;

FIG. 12A is a bottom (incisal) plan view of the teeth of FIG. 1.1A;

FIG. 12B is a bottom (incisal) plan view of the teeth, magnets, metal plates and aligner of FIG. 11B;

FIG. 12C is a bottom (incisal) plan view of the aligned teeth of FIG. 12C;

FIG. 14C is a diagrammatic view of a set of selected teeth and one tooth bracket having a longer bracket post for transmitting (and mimicking a step-in bend) tooth-moving forces to that tooth from a nitinol archwire;

FIG. 14D is a side elevational view illustrating a bent post that can be adjusted by an orthodontist to increase or decrease its length between the archwire bracket and the tooth mounting plate as desired;

FIG. 14E is a top plan view of the arrangement of FIG. 14D, illustrating the bent bracket post in an initial distance from the tooth and with the distance adjusted (in phantom lines) to increase the initial distance;

FIG. 14G is a perspective view, taken from the top of a tooth bracket that utilizes a post-style construction for engaging the tooth mounting plate;

FIG. 14H is a top plane view of the arrangement of FIG. 14G, illustrating the complementary-shaped structure of the tooth mounting plate and the wire bracket mounting end;

DETAILED DESCRIPTION OF THE DISCLOSURE

While the present disclosure may be susceptible to embodiment in different forms, there is shown in the Figures, and will be described herein in detail, specific embodiments, with the understanding that the disclosure is to be considered an exemplification of the principles of the present disclosure, and is not intended to limit the present disclosure to that as illustrated.

In the illustrated embodiments, directional representations—i.e., up, down, left, right, front, rear and the like, used for explaining the structure and movement of the various elements of the present disclosure, are relative. These representations are appropriate when the elements are in the position shown in the Figures. If the description of the position of the elements changes, however, it is assumed that these representations are to be changed accordingly.

Figure 1A:
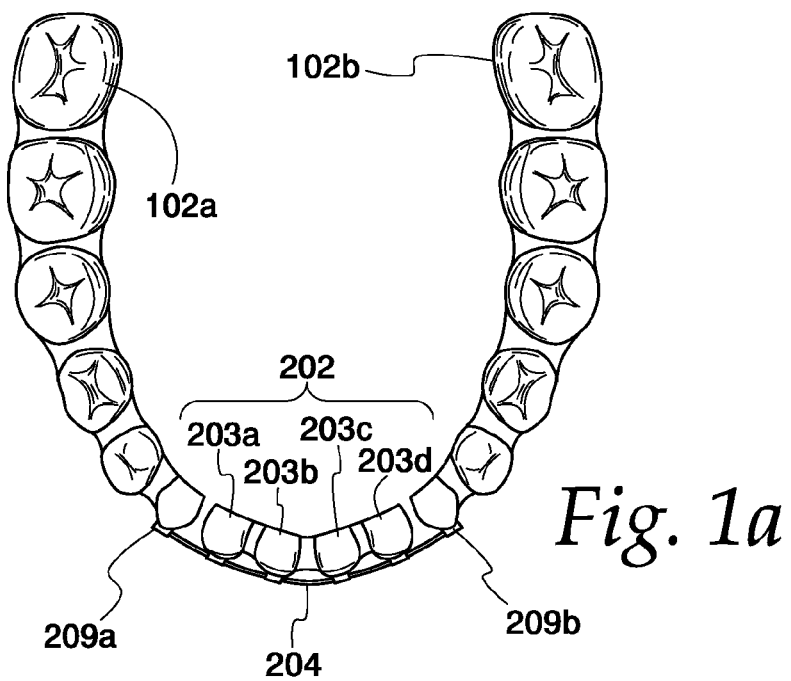
FIG. 1A is a top plan view of a some of the components utilized in the present disclosure for moving a patient's lower anterior teeth, including a pair of resin trays molded in a manner to move and straighten the patient's and joined together by way of an archwire adapted to contact, move and straighten the patient's front teeth.

Turning to the Figures and to FIG. 1A in particular, a top plan view of a part of a system for moving teeth is illustrated. In specific, FIG. 1A depicts the components of the system adapted for straightening the lower teeth of a particular patient. Two of the components are a lower left tray 102a and a lower right tray 102b. The component also comprises an upper left tray and upper right tray that are not depicted. Each of the trays is especially formed to mate with a particular set of multiple teeth; i.e., the lower left teeth of a patient, the upper right teeth of a patient, etc.

Each of the trays 102a, 102b can fit over the rear teeth of a quadrant of a patient's jaw. Generally, the rear teeth of a patient will require less correction than the front teeth of the patient; i.e., they will be in better alignment than the front teeth. The trays 102a, 102b can be formed of a polymeric plastic, or a dental resin, including materials that are safe for use in a patient's mouth as are known in the art. The polymeric plastic can be clear or white in color for aesthetic purposes.

FIG. 1A also depicts a set of tooth caps 202 which are adapted to fit over the teeth of a particular patient that need movement as determined by patient's orthodontist. As with the trays, the set of caps 204 is especially designed to go over a particular patient's teeth. Each of the tooth caps 203a-d is joined to the other tooth caps by an archwire 204. A pair of distalmost support brackets 209a and 209b are disposed at the ends of the archwire 204 and attached to the two trays 102a, 102b at the forward portions thereof. The distalmost support brackets are placed to provide anchorage and accept slack in the archwire, thereby protecting the patient from scratches and cuts as the archwire lengthens due to the patient's teeth straightening. The most distal brackets 209a and 209b are disposed on the lower left tray 102a and lower right tray 102b respectively, thereby allowing the entire system to be snapped in and out by a patient as a single apparatus. As illustrated in the Figures, the rear trays 102a, 102b and the individual tooth caps are interconnected together as a single assembly by the archwire 204 that will engage either the top or bottom teeth.

Figure 1B:
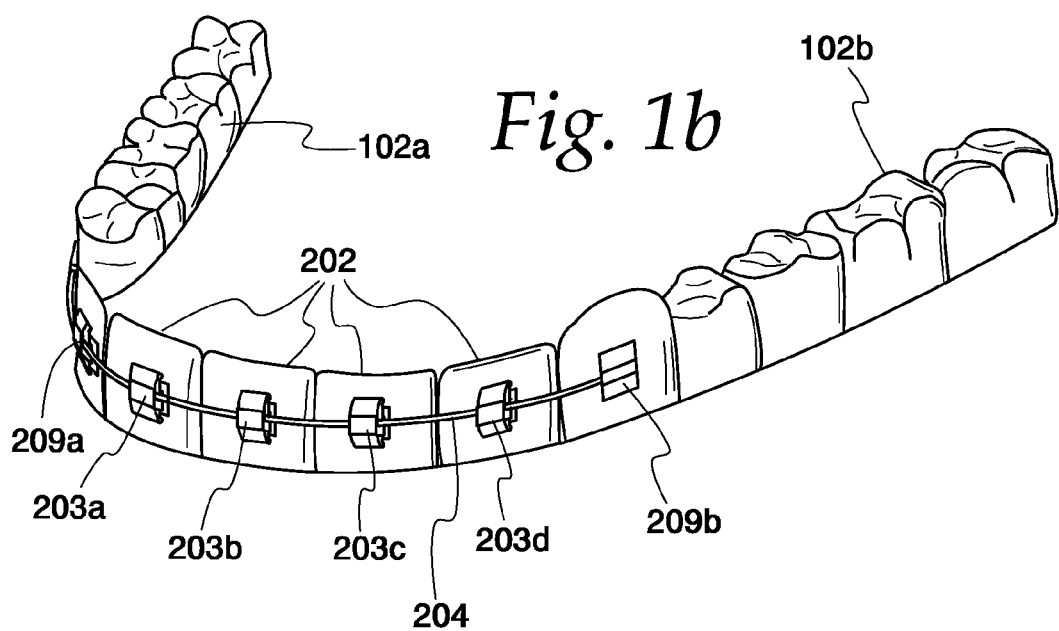
FIG. 1B is a perspective view of an orthodontic assembly constructed in accordance with the principles of the present disclosure for use in arrangements for moving a patient's lower teeth in a preselected pattern.

FIG. 1B depicts a perspective view of the components of the disclosed teeth straightening system used to straighten a patient's lower teeth. As with FIG. 1A, a set of trays 102a, 102b adapted to straighten a particular patients teeth are provided. In addition, a set of tooth caps 202 adapted to straighten selected ones of a patient's front teeth is provided.

Each of the individual tooth caps 203a,b,c,d in the set of caps 202 is joined together as an assembly, by an archwire 204, at the ends of which are a pair of distal most support brackets 209a,209b. The distalmost support brackets 209a, 209b are preferably disposed forward of the back of a patient's mouth so that as the patient's teeth straighten and additional slack in the archwire 204 is created, the slack will not reach a dangerous length unless not addressed for a very long time. In FIGS. 1A and 1B the caps 202 are joined to trays 102a and 102b by way of brackets 209a and 209b. This should greatly reduce or even eliminate emergency trips by patients to the orthodontist that use the disclosed system for moving teeth. Each of the tooth caps 203a-d can be constructed of a polymeric plastic similar to what is used to make aligners, or other material safe for use in a patient's mouth, such as a dental resin or other materials known in the art. The polymeric plastic can be clear or white in color for aesthetic purposes.

Figure 2A:
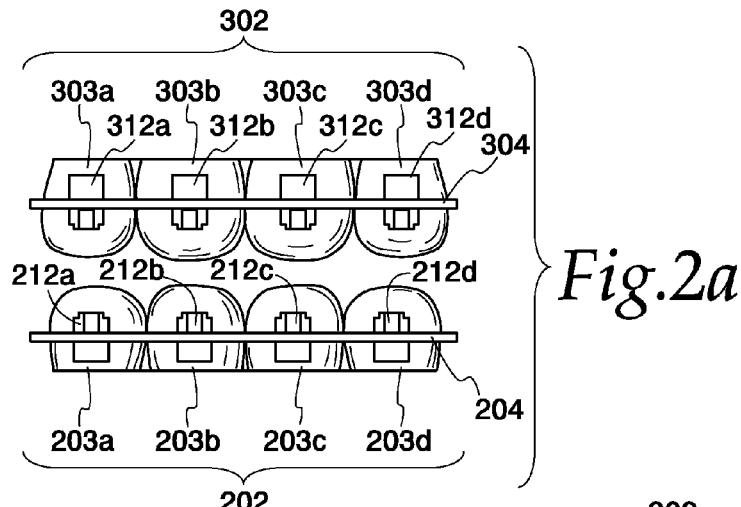
FIG. 2A is an enlarged front elevational view of a set of caps applied to upper and lower teeth, wherein the caps are joined together by an archwire adapted to move and straighten a patient's front teeth, and wherein the support brackets thereof mounted on the tooth caps are illustrated in an open position.

FIG. 2A illustrates a front view of a complete set of tooth caps 202, 302 constructed in accordance with the present disclosure, with each cap 203a-d, 303a-d incorporating an orthodontic support bracket 212a-d, 312a-d attached to the front portion of each tooth cap. As depicted each set of tooth caps 202, 302 is constructed to mate respectively with the front four upper and lower teeth of a patient. It should be noted that the same design could also incorporate other teeth, such as the front six upper and lower teeth of a patient. In particular, the tooth caps designed to fit over the patient's lower teeth are denominated as 203a-d and the tooth caps designed to fit over the patient's upper teeth are denominated as 303a-d. As illustrated, the brackets 212a-d, 312a-d in FIG. 2A are in an open position, allowing an archwire 204, 304 to be inserted into engagement portions of the support brackets 212a-d, 312a-d, removed from the brackets 212a-d, 312a-d, or to be adjusted as needed. It should be noted that individual tooth caps will be only made for teeth that require movement (in most cases they will be anterior or front teeth) as well as the teeth that are mesial and distal to those that require straightening. Rear teeth that do not require substantial movement or straightening will utilize a tray 102a, 102b as described above.

Figure 2B:
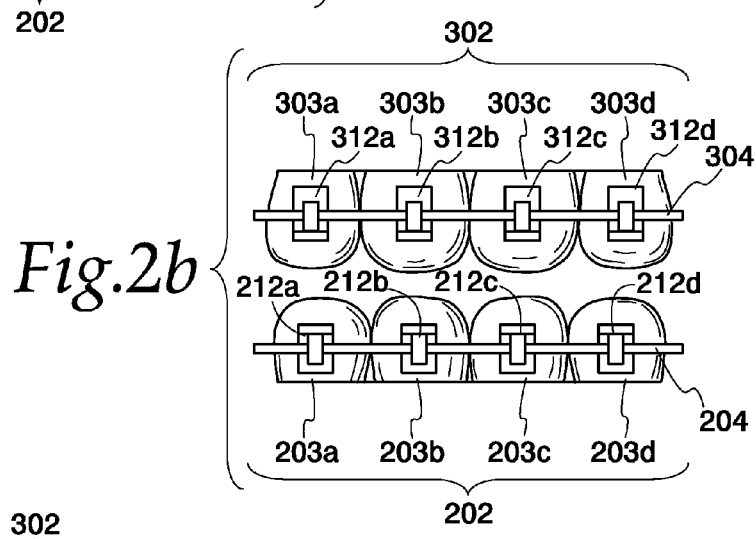
FIG. 2B is the same view as FIG. 2A, but where the support brackets mounted on the tooth caps are illustrated in a closed position.

FIG. 2B is the same as FIG. 2A, except that the support brackets 212a-d, 312a-d are shown in a closed position so that the archwires reliably engage the tooth caps and thereby indirectly engage the teeth disposed in the tooth caps.

Figure 2C:
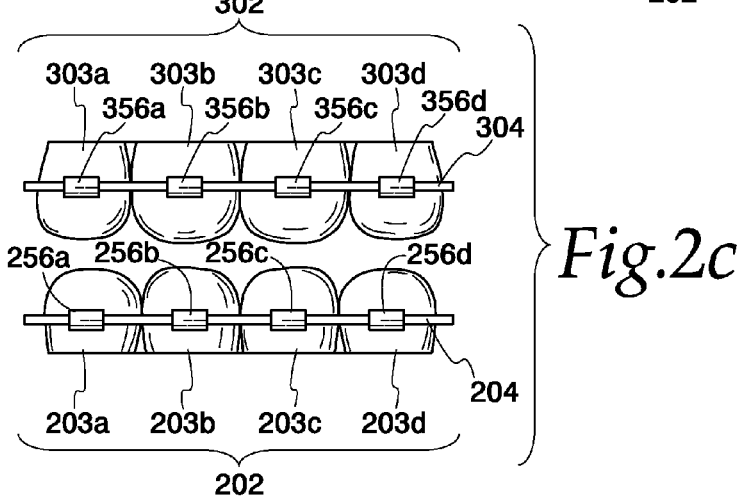
FIG. 2C is the same view as FIG. 2A, but illustrating a series of hollow tubes or inbuilt aligner holes used as the support brackets on the tooth caps.

FIG. 2C illustrates an alternative embodiment of the set of tooth caps 202, 302, wherein each tooth cap 203a-d, 303a-d has an archwire support in the form of an attached tube 256a-256d and 356a-356d disposed on it. Alternatively, the tooth caps may be provided with embedded tubes or the like through which the archwires pass. In particular, tooth caps 303a-d have corresponding tubes 356a-d formed on the front of them (or into them), and tooth caps 203a-d have corresponding tubes 256a-d formed into the front of them. Each tube 256a-d, 356a-d can be formed of the same material as the caps 203a-d, 303a-d. Alternatively, the tubes 256a-d, 356a-d can be metal that is bonded to the front of the caps 203a-d, 303a-d using any prior art method of bonding metal to plastic that is safe for use in a patient's mouth. The metal comprising the tubes 256a-d, 356a-d can be white in color for aesthetic purposes.

FIG. 3 illustrates a single tooth cap 403 with a support bracket 412 attached to it. The support bracket 412 can be constructed in accordance with any prior art method, such as that disclosed in U.S. Pat. No. 5,466,151, which is hereby incorporated by reference in its entirety. As illustrated, the bracket support 412 comprises a support base 410 having a posterior surface 411 which is bonded to the tooth cap 403 using any prior art method of bonding a metal surface to a plastic surface that is safe for use within a patient's mouth.

A pair of tying lugs 434 project anteriorly from base 410. Each lug 434 includes opposed extensions 413 and 414 that project outwardly between transversely spaced side surfaces formed on the bracket 412. These lugs each include an outer side surface 415.

The bracket 412 also includes an anterior surface 417 across the front of each lug 434. The anterior surface 417 is illustrated as being planar, but can be curved as well. It is interrupted by the opening of a transverse archwire slot 422 that is formed distally from the anterior surface 417. The archwire slot 422 spans the full width of the bracket 412.

The archwire slot 422 includes side slot surfaces 418 and an anterior slot surface 420. The slot surfaces 418 and 420 are sized to accept an archwire (not shown). A closure complementary to the archwire slot 422 is also provided with the support bracket 412. It includes a movable cover 421 that slidably engages the anterior surface 417. Cover 421 has a width that spans the full width of the tying lugs 434. Its perpendicular width is greater than the corresponding width across the archwire slot 422 at the anterior surface 417 of the bracket 412. Typically, the archwires 204, 394 will substantially fill the archwire slots 422 of the support bracket 412. As illustrated, the support brackets 412 serve to hold the archwires 204, 304 in their extent along the anterior surfaces of the patient's teeth.

The disclosed system is intended to be used by orthodontists in treating their patients. The first step in using the system is to obtain a representation of the patient's teeth. The representation can be obtained, for example, by using x-rays, three-dimensional x-rays, computer aided tomographic images, magnetic resonance images, or other means. However, the usual way of obtaining a representation of a patient's teeth will be to take a PVS impression or digital dental scan of patient's teeth using well known techniques. Once the impression is taken, a digital representation can be made if desired. The digital representation can be used to create a set of trays to translate the patient's back teeth, both lower and upper, from their initial position to the planned straightened position. As many persons will have relatively straight posterior teeth, generally only one set of trays will be required to translate their back teeth into alignment. In other cases, two or multiple trays will be deemed necessary to align teeth into a desired occlusion.

In addition, the digital representation can be used to create the initial sets of caps, and plan the length of the archwire 204, 304 used to join the tooth caps and produce straightening force upon a patient's front teeth.

Turning to FIGS. 4A, 4B and 5, the structure of the tooth caps 202, 302 are explained. As shown in FIG. 4A, a tooth 50 has a lower root portion 52 that is embedded in a patient's mouth, and an upper crown portion 54 that is exposed in a patient's mouth. The crown portion 54 of each tooth has a unique exterior configuration which lends itself to the assemblies of the present disclosure. The tooth caps 202, 302 of the present disclosure are configured in the form of a hollow shell 55 that includes an exterior shell portion 56 that encloses a hollow interior in the form of a cavity 57. The hollow interior 57 of the tooth cap 202, 302 is preferably complementary in configuration to its corresponding tooth 50 so that a tight fit is obtained when the shell portion 56 is applied to the tooth crown portion 54.

In instances where the configuration of the tooth 50 is such that the shell portion 56 of the tooth cap 202 can move relative to the tooth crown portion 54, a retention lug 58 may be applied to the tooth crown portion 54, as illustrated in FIG. 4B. The retention lug 58 is preferably formed from a composite material and is bonded to the tooth crown portion 54. The retention lug 58 extends outwardly so that it is received within a corresponding cavity 59 formed in the tooth cap shell portion 56 in opposition to the retention lug 58. This structural interaction serves to assist in the retention of the tooth cap 202 on the tooth 50. As illustrated in FIG. 5, wire guides 60 may be provided and are fixed, preferably by bonding, to the tooth cap shell portion 56 in order to provide an anchor point for the archwire 204, 304. The wire guides 60 may include support brackets as described at 412 above, or they may include hollow metal tubes 62 that have their central openings oriented transversely or at an angle to the vertical axes of the tooth caps to which they are applied so that the archwire may be passed through them.

As can be understood by the disclosure, the tooth caps are applied to the selected teeth that need to be aligned or straightened and they are interconnected to the rear teeth trays of the assembly. Thus, the entire assembly may be removed from the upper or lower teeth when the patient needs to brush or floss. The tooth caps are configured to securely and reliably grip their corresponding teeth. Loose ends of the archwire will not present a problem as they will lie against the surfaces of the trays or tooth caps and will usually occur farther back in the mouth. The tooth caps, may in some instances be configured to contact more than one tooth, but the advantages of the assemblies of the present disclosure are greatest when the tooth caps are applied to individual teeth.

Figure 6:
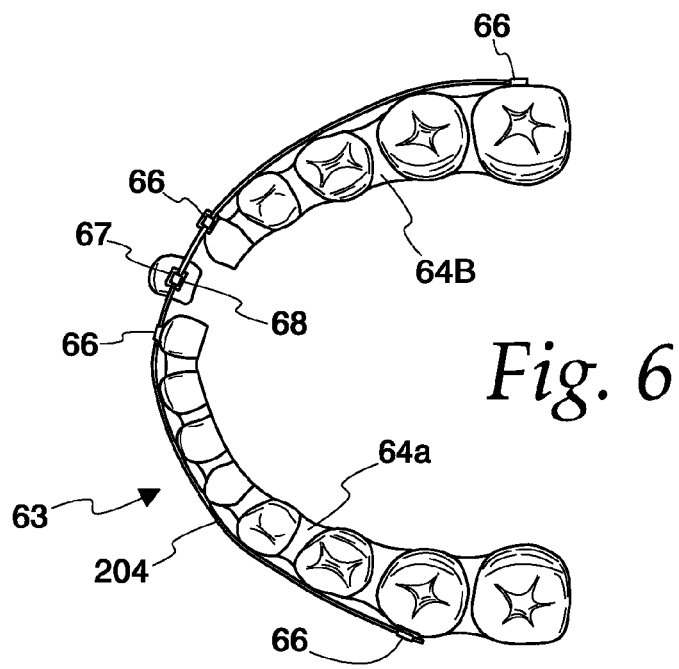
FIG. 6 is a top plan view of an alternate embodiment of an orthodontic assembly in accordance with the present disclosure illustrating a pair of rear teeth trays and a tooth cap interposed therebetween and interconnected by an archwire utilizing magnetic force to hold the archwire in place on the assembly to align a single central incisor.

FIG. 6 is a plan view of another embodiment of an orthodontic assembly 63 that utilizes two teeth trays 64*a*, 64*b* and one tooth cap 65. An archwire 204 is provided and is captured in support brackets 66 fixed to the teeth trays 64*a*, 64*b*, and is also captured in a support bracket 67 fixed to the tooth cap 65. The archwire serves to define a limit position for movement of the teeth. In the embodiment illustrated, at least the tooth cap support bracket 67 takes the form of a tube 68. As such, FIG. 6 illustrates the structural advantages of orthodontic assemblies of the present disclosure, specifically, how the individual tooth caps 65 are permitted to move relative to the teeth trays 64*a*, 64*b*. Such movement in this instance is mostly rotational movement about the archwire 204. This permits the single tooth cap 65 to be moved into secure and reliable engagement with its corresponding tooth independent of the position of the rear teeth secured by the teeth trays. This structure ensures that the position of individual teeth in a patient may be performed on an incremental basis and that the tightening of the archwires is performed on a patient in a more comfortable manner than with braces applied directly to the patient's teeth.

Figure 7:
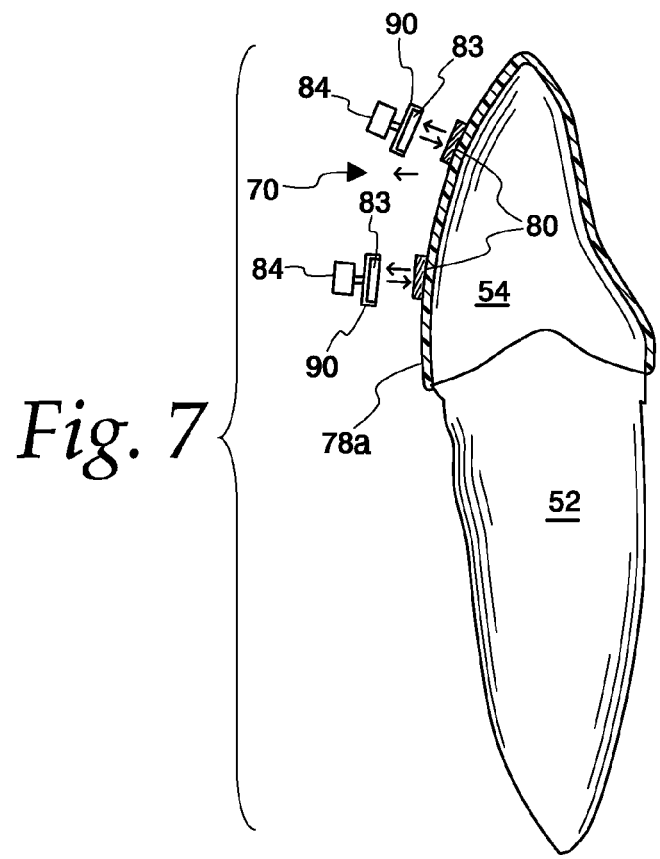
FIG. 7 is a side elevational view of a single tooth with a tooth cap in place thereon, illustrating metal anchor pads and magnetic brackets in opposition to each other.
Figure 8:
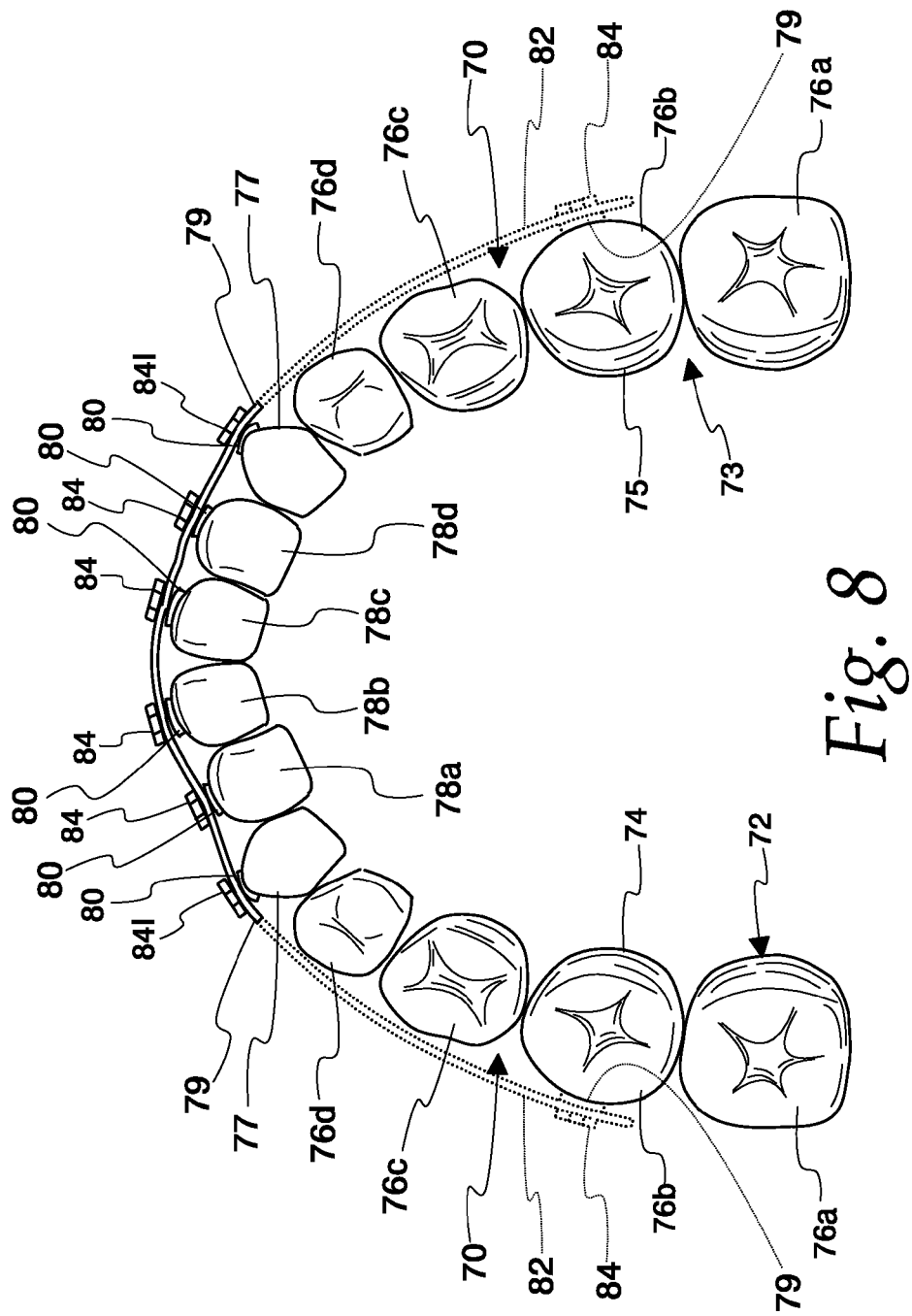
FIG. 8 is a top plan view of a orthodontic assembly in place in accordance with the present disclosure in place on a set of teeth, with two teeth trays extending over the molar and canine teeth and individual tooth caps in place over the incisor teeth

FIGS. 7 & 8 illustrate an assembly 70 of the present disclosure that is configured to attach to multiple teeth of either the upper or lower set of teeth of a patient. Two teeth trays 72, 73 are present and they utilize molded, or otherwise formed, continuous shells 74, 75 that extend over the molar teeth 76*a-d* and, as shown, over the adjacent canine teeth 77. As noted from this description and from the Figures, the opposing ends of the archwires are affixed to the teeth trays by way of their corresponding support brackets. Individual tooth caps 78*a-d* are provided (four in number) and are disposed between the forward ends of the teeth trays 72, 73 and adjacent the canine teeth 77, as illustrated. The teeth trays 72, 73 may be provided with metal engagement surfaces, or pads 79, and the tooth caps 78*a-d* may also be provided with similar metal engagement pads 80. The engagement pads 79, 80 are bonded respectively to the teeth trays 72, 73 and tooth caps 78*a-d* in manners known in the art. In instances where the canine teeth need to be aligned in a patient's mouth, the teeth trays will end at the molar teeth and the support brackets associated therewith will be in opposition to molar teeth in contrast to FIG. 1B where the trays are shown as ending at the canine teeth of the patient.

In one aspect of this illustrated embodiment, an archwire 82 is held by a series of wire guides 84 that have channels that receive portions of the archwire 82 therein. These wire guides 84 can either be magnetized (or formed from a magnetic material) so that they magnetically engage the engagement pads 80, or they may have magnets 83 respectively inserted in their base portions 90, for engaging the metal pads 80. In another aspect of this embodiment, the two end wire guides 841 may be directly bonded to the teeth trays 72, 73 at the canine teeth 77 thereof. The four wire guides 84 which are for use on individual incisor teeth are spaced apart on the middle of the archwire 82 between the end wire guides 841. They are magnetized or have magnets integrated therewith as part of their structure and as noted above. In this fashion, they can magnetically engage the metal pads 80 bonded to the incisor tooth caps 78*a*-dand exert tooth movement forces on selected teeth. A second archwire may be used as illustrated and will require its own associated wire guides 84 and tooth engagement pads 80 bonded to the teeth.

The magnetic force should be enough to securely and reliably engage the metal pads 80 to thereby force movement of the teeth in the tooth caps 78*a-d* in an incremental fashion as called for in the plan of treatment for the patient. Permanent magnets, such as Alnico, Neodymium and rare earth magnets provide good magnetic engagement forces in the range of from about 50 grams up to about 400 grams of contact force, with about 100 grams of contact forces being normally used. The wire guides 84 utilized on the individual tooth caps are positioned in opposition to particular teeth for moving, i.e., to move an incisor, the support bracket must engage the incisor tooth cap, etc. The archwire 82, when tightened, will coerce the teeth in the tooth caps 78*a-d* to move. This process usually involves a series of incremental movements, each of which requires tightening of the archwires 82.

Figure 9:
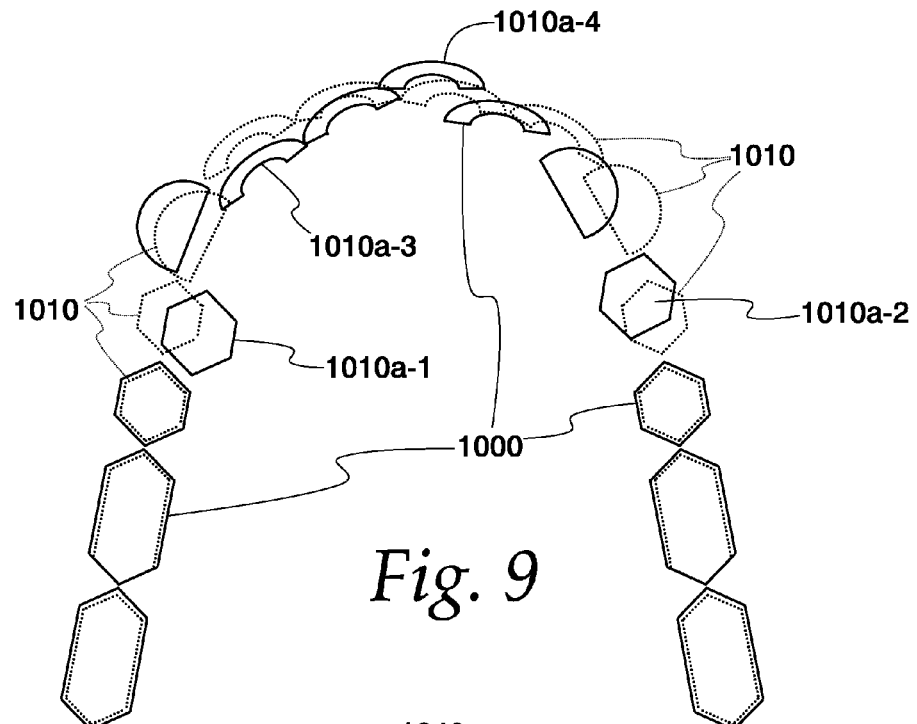
FIG. 9 is a top plan view of the lower teeth of a patient, with the out of alignment positions shown in solid lines and the position to which the teeth shall be moved in dashed line.

FIGS. 9 through 12C illustrate yet another embodiment of an orthodontic appliance in accordance with the principles of the present disclosure in which the teeth moving members are supported by an aligner. FIG. 9 is a top plan view of a patient's lower set of teeth. The teeth 1000 are depicted in their out-of-alignment position in solid lines, while the dashed lines in FIG. 9 indicate the final position 1010 of the teeth 1000 as decided upon by the orthodontist. In order to move selected teeth 1010*a* into their final positions, an aligner system is utilized that includes an outer, hollow shell 1020 formed preferably from an aligner material (thermoplastic) or a suitable resin. The aligner shell 1020 is shown as extending the entire length of the set of teeth, from rear molar to rear molar. The shell 1020 preferably includes additional space(s) 1021 surrounding the teeth 1010*a* that need to be moved. The additional space 1021 provides space for each such tooth 1010*a*-1 to 101*a*-5 to move within the shell 1020, and also accommodates the teeth-moving elements 1030 such as metal plates 1040, or magnetic plates 1050. The teeth moving elements may be adhered, or otherwise attached, to the shell 1020 or they may be molded, or embedded, in place therein during fabrication of the shell 1020.

Figure 10:
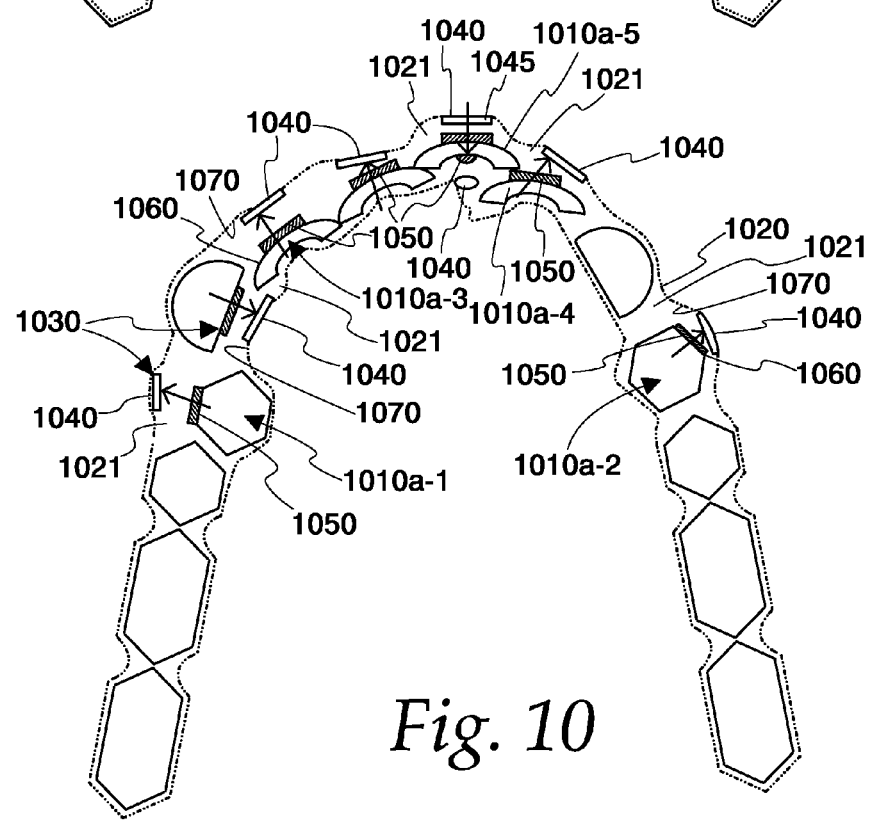
FIG. 10 is a top (incisal) plan view of the lower teeth of a patient with the teeth occupying the out of alignment positions shown in FIG. 9, and covered with a aligner tray in accordance with the present disclosure, which extends to cover all of the lower teeth, and further illustrating the desired movement of the teeth under magnetic movement as well as placement of the tooth moving elements on the aligner and selected teeth.

FIG. 10 illustrates the hollow shell 1020 with the teeth-moving elements 1030 in place therein. For some teeth, such as 1010a-1, a metal engagement plate 1050 is bonded to the exterior surface 1060 of the tooth 1010a-1, and a magnet 1040 shown in the form of a magnetic plate is disposed on an interior surface 1070 of the shell in opposition to the metal plate 1050. The shell 1020 is formed after taking an impression of the patient's particular set of teeth. Based on the desired alignment and choice of an orthodontist, the shell 1020 may be sculpted to provide specific surfaces in the form of seats for the magnets 1040 in order to provide a path for the desired movement of a particular tooth. The shell 1020 illustrated extends across the entire set of lower teeth, from rear molar to rear molar as in a series of interconnected tooth-receiving cavities in order to provide a support sufficient to address all of the lower teeth which need alignment. It will be understood that the shell may also only extend over a selected set of teeth, as is shown in FIGS. 11B and 12B. In this regard, pairs of tooth moving elements comprising magnets 1040 and metal engagement plates 1030 are preferably arranged together in direct confronting relationship, such as in a generally parallel arrangement as shown with teeth 1010a-1 and 1010a-3, or the pairs may be slightly offset at an angle, as with teeth 1010a-2 and 1010a-4, so as to move the teeth in an offset, or angled path of alignment.

The magnets 1040 man be embedded inside of or on the outside of the aligner shell 1020 and exert tooth movement forces on selected teeth of preferably between about 50 grams and about 400 grams of force. In most instances, the magnets 1040 will primarily exert a magnetic attraction type of tooth movement force, drawing the selected tooth toward the magnets 1040 by way of attraction to the metal engagement plates 1050 bonded to the teeth. This is shown in FIG. 10 for teeth 1010a-1, 1010a-2 and 1010a-3. Although the shell 1020 in FIG. 10 is illustrated as having its magnets supported on the shell, it will be understood that the shell may also support the metal plates and the teeth support magnets. The aligner and teeth may also support both types of tooth moving elements. The magnets 1040 may also be used to secondarily exert repulsion type of tooth movement forces, such as illustrated in FIG. 10 on tooth 1010a-5, where one magnet 1040 is shown affixed to the shell 1020, and another magnet 1045 is bonded to the tooth 1010a-5. These two magnets are oriented to display a repulsion force against each other following the arrow in FIG. 10. A reverse alignment of 1045 will result in stronger attraction force between magnets if desired by orthodontist. A metal engagement plate 1050 may be bonded to the backside of the tooth 1010a-5 so that it is attracted to an additional magnet 1040 spaced behind it in the shell 1020. In this manner, it can be seen that multiple magnetic forces may be exerted on selected teeth for specific movement, rather than just a movement and force which a single magnet-metal plate arrangement would provide.

As noted above, all of the tooth moving elements on the aligner shell may be magnets with the corresponding metal plates applied to the teeth, or all of the aligner elements may be metal plates with the corresponding magnets applied to the teeth. The aligner may include assorted magnets and metal engagement plates while the teeth may include a similar, but opposite assortment of tooth moving elements to form distinct pairs of tooth moving elements. FIGS. 11A-12C illustrate variations of the embodiment of FIGS. 9 & 10, and use a smaller aligner shell 1020 of the disclosure that is fashioned with fewer teeth-receiving cavities and which has a length sufficient to align only the front (incisor) teeth 1000 of a patient. FIGS. 11A-11C illustrate how the two outside teeth 1010a-6 and 1010a-7 may be drawn down into their desired locations. This is done by applying the magnets 1040 to interior surfaces 1070 of the shell 1020 so that they are positioned underneath their corresponding metal engagement plates 1050 attached to the teeth so that the attraction force between the magnets 1040 and the metal engagement plates 1050 occurs in the downward direction. The magnets may be disposed in nest formed in the shell, or may also be formed with the shell.

FIGS. 12A-12C illustrate the use of magnetic repulsion forces as tooth movement forces. In this type of treatment, pairs of magnets 1040, 1045 are used and the first magnets 1045 are attached to the middle teeth on the lingual surfaces thereof. The second magnets 1040 (of reverse polarity than the first magnets 1045) are supported on the interior surfaces 1070 of the shell 1020, in opposition to and confronting the first magnets 1045 to control the position and movement of the middle two teeth. This embodiment utilizes the repulsion force between two magnets 1040, 1045 to provide the tooth movement forces and these forces can be larger than magnetic attraction forces between the magnets 1040 and corresponding engagement plates 1050. In this manner, the orthodontist can design the alingers of the present disclosure to apply different magnitude tooth movement forces to different individual teeth in accordance with a custom treatment regimen.

The metal engagement plates 1050 (and the corresponding magnets) may be provided in white so as to lessen the visual impact of the appliance on the patient, and the aligner shell 1020 may be formed in a transparent fashion to let the patient's teeth show through it. As noted earlier, the aligner shell (appliance) 1020 is removable by a wearer, so that normal hygiene procedures may be followed or the aligner shell removed for social events.

Figure 14:
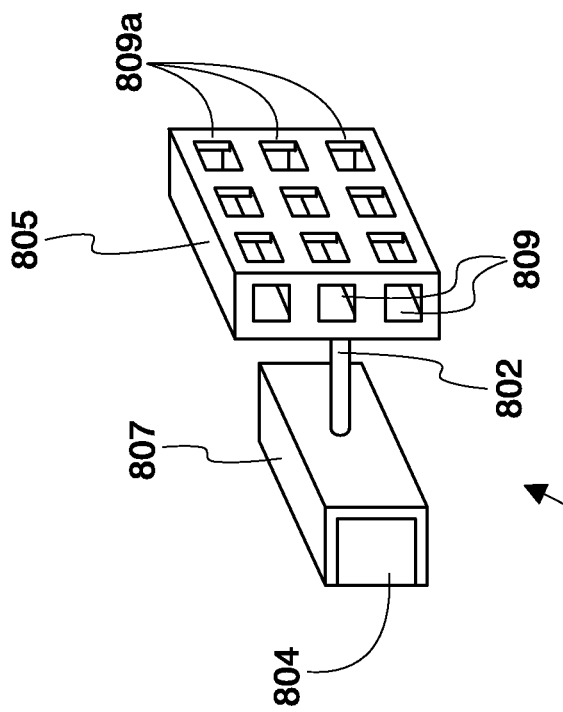
FIG. 14 is a perspective view of an archwire bracket of the present disclosure with multiple archwire slots and an adjustable length piece formed therein.

FIG. 14 illustrates, in a perspective view, an orthodontic bracket system 800 that may be utilized in appliances of the present disclosure and which has particular utility apart from the use of aligners. The bracket assembly 800 includes a magnet 804, which may be provided as an individual component, or it may be held within a housing 807 that is formed as part of the bracket assembly 800. The housing 807 is attached to a wire guide member 805 that includes a plurality of wire-engaging slots 809, each of which is structured to receive a portion of an archwire 808 therein and which also include end bars 809a for retaining the archwire 808 in one or more of the slots 809. Three such wire-engaging slots 809 are illustrated, but there may be more or less, depending on the course of treatment, and the slots 809 are shown as extending horizontally, but vertically spaced apart. The wire guide member 805 and the magnet-housing portion 804/807 of each bracket assembly 800 further includes a post 802 joining these two components together as a single structure. The posts 802 may be vertical or horizontal or of a varying length as well as curved, to provide certain advantages as explained in detail below.

Figure 14A:
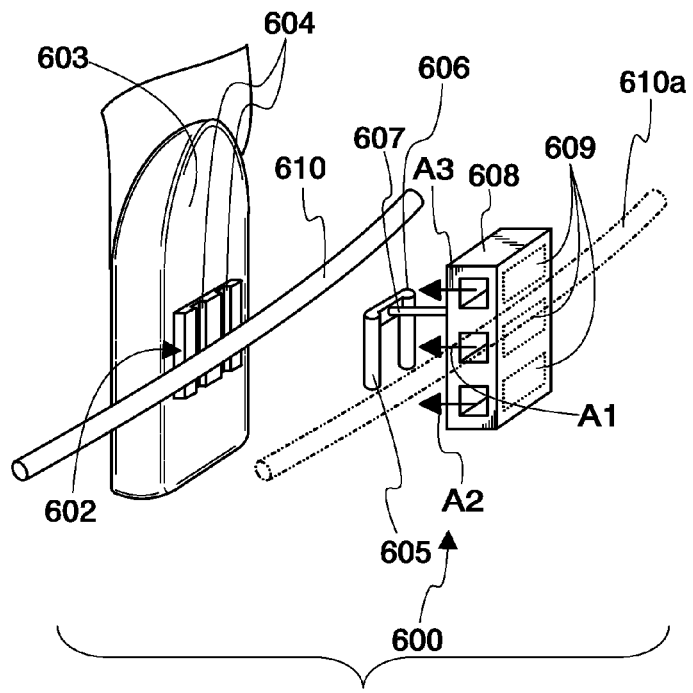
FIG. 14A is a diagrammatic view of a tooth, a base plate, a guide wire bracket and a nitinol archwire, illustrating the original shape of the archwire, with the installed shape of the archwire extending through one of the bracket slots, and the lines of application of tooth moving forces that can be applied with use of such a bracket.

FIG. 14A illustrates another style of bracket assembly 600 of the present disclosure in which a plate or the like 602 is attached to a tooth 603. The plate 602 may be formed from metal, plastic, ceramic or other suitable materials and is configured with one or more channels 604 which are shown as extending generally vertically therein. The channels 604 receive lugs 605 of a base member 606 that is shown as having a general inverted U-shape. The base member 606 has a stiff post 607 that extend outwardly (vertically or horizontally) therefrom and which is connected to a wire guide member (orthodontic bracket) 608. This wire guide member 608 also has a plurality of wire-engaging slots, arranged generally horizontally and which are individually configured to receive a portion of an archwire 610 therein and which may have widths of between 0.018 and about 0.022 inches. In this embodiment, the multiple wire-engaging slots 609 can engage a flexible nitinol wire instead of a rigid stainless steel archwire. The wire guide member 608 has a base that includes multiple lengthwise slots 609. The slots 609 may include associated retaining bars 635 that serve to retain the archwire 610 in place within the slots. This may also be done with appropriate latch members.

The nitinol wire as noted above is a memory shape alloy wire that can be first bent or otherwise configured into a baseline shape, shown in solid lines at 610 in FIG. 14A. The wire may then be installed in a patient's mouth, engaging the wire guide members 608 in selected slots 609 thereof taking a different configuration than the original baseline shape. This different, installed configuration is illustrated in phantom at 610a in FIG. 14A. The heat of a patient's mouth will activate the wire and it will tend to return to its baseline position and exert tooth moving forces on selected teeth The lines of action of these forces are shown by arrows A1, A2, A3 in FIG. 14A and the orthodontist may choose a particular slot in this embodiment to receive the nitinol wire in order push in or pull out a tooth, without resorting to forming step in or step-out bends in the archwire as is done in use with rigid stainless steel wires. The slots 609 may also be used to effect drawing teeth up or down in the vertical direction as is done with rigid archwires using step-up and step-down bends.

Figure 14B:
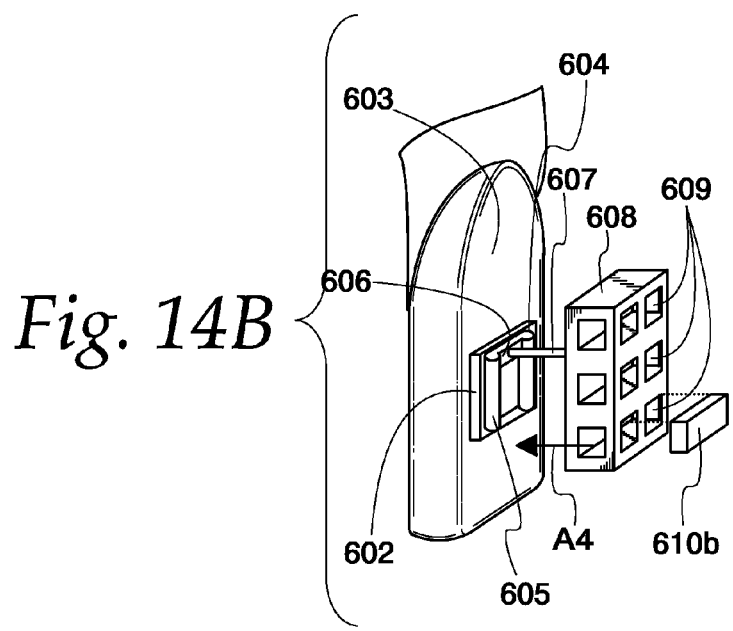
FIG. 14B is a diagrammatic view of a bracket engaged to the base that is attached on a tooth at an angle illustrating how the bracket and archwire can be used for applying torque tooth-moving forces to selected teeth.

FIG. 14B illustrates the use of the wire guide member 608 of FIG. 14A that is mounted to a tooth in order to apply torque to the tooth 603 and the root of the tooth. In this structure, the post 607 is angled upwards with respect to the tooth plate 602, so that when an archwire 610b is bent into an engagement shape for a set of teeth, it can also be bent to return to its original shape in a fashion that will apply a moment to the tooth 603. The archwire 610b is preferably formed with a non-circular cross-section, such as a rectangular or square cross-section so that the archwire will not rotate in the wire guide member slot 609. Rather, the archwire 610b engages the wire guide member 608 firmly so as not to rotate. In this manner, when the archwire 610b is inserted into the bottom slot of the wire guide member shown in FIG. 14B, the archwire transfers a tooth moving force to the tooth that is non-linear. In this structure, the archwire 610b will create a clockwise moment about the plate 602 attached to the tooth in the direction of the arrow A4. This will tend to move the bottom of the tooth inwardly and also exert a turning force on the tooth root (at the top of the tooth). The top, middle and bottom slots may be chosen based on their location relative to the wire guide member post 607 to apply a desired torque force to selected teeth.

FIG. 14C illustrates how the bracket assembly 608a may be modified to exert a particular force on one tooth 603a of a set of selected teeth 603. The one tooth, 603a, needs to be pushed in (to the left in the Figure) and in order to so with conventional braces, the orthodontist would form a step-in bend in a rigid stainless steel archwire. However, in using a flexible nitinol archwire, the post 607a of the wire guide member 608a is made longer than the corresponding other posts 607 and has a length of L2 as compared to the length L1 of the other posts 607. The nitinol archwire 610 will have an outward bend in it in order that it engages the one wire guide member 608a in one of the slots 609 thereof, and in an outward curve as shown in the detail inset in the lower right of FIG. 14C. When activated by placing the wire in patient's mouth, it will tend to return to its original shape, shown at 610" in phantom in the inset. The nitinol wire 610 will consequently exert a greater inward pushing force on tooth 607a than on the other teeth 603 that flank the one tooth 603a. In this manner, the need for a step-in bend is eliminated as is the use of rigid archwires, to thereby alleviate patient discomfort. Retainers in the form of latches 635 may be provided to retain the archwire 610 in the selected slots 609 and these members may be either fixed in place on the brackets as shown earlier, or movable, so that it may be manipulated by the orthodontist.

The posts 607 used in the bracket assemblies need not be straight or linear in their extent with fixed distances. FIGS. 14D and 14E illustrate another wire guide post structure where the post 607b is bent at an angle between the attachment plate 602 and the wire guide member 608. The bend in the post 607b permits the orthodontist to shorten or lengthen the post as shown by the extension of the post 607c in phantom. Reducing the rise of the bend (and increasing the included angle of the bend) will lengthen the post distance from B1 to B2 as shown, while increasing the rise of the bend (and decreasing the included angle of the bend) will shorten the post distance between the attachment plate and the wire guide bracket. In this manner, with assemblies of the present disclosure, an orthodontist can adjust the length of the post 607 with his pliers and thereby adjust the tooth moving force that it transfers from a corresponding wire guide member 608 to a selected tooth 603b. The orthodontist can further rotate the wire guide bracket 608, if desired, by turning the post 607. In this regard, the post 607 is preferably formed from a durable stainless steel, or alloy thereof that is flexible to be moved using pliers, but stiff enough to maintain a durable position of the wire guide bracket without shearing or degrading, The mounting plate 602 used to mount to a tooth 603b may include, as illustrated in FIG. 14F, a plurality of pockets 602a formed in its tooth-contacting surface which can be filled with an adhesive when the mounting plate 602 is adhered to a tooth.

FIGS. 14G and 14H illustrate another bracket arrangement where the wire guide member 608 has a bent post 607b, but the post 607b is formed so as to be engageable and removable from a tooth mounting plate 640. In this regard, the tooth mounting plate 640 has openings 641, 642 that are sized to receive posts 643, 644 of the port 607b so that the bracket and post, 608, 607b may be disengaged by the orthodontist and removed from the patient. Two of the posts 643 are received in circular openings 641 and the remaining post 644 is received in a channel 642

Figure 15A:
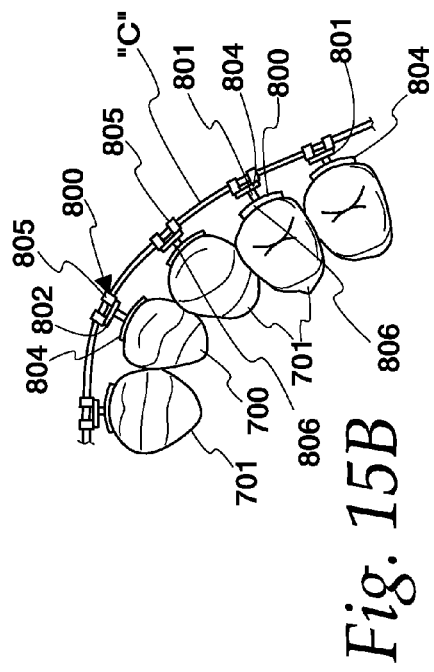
FIG. 15A is a partial top plan view of the right lower teeth of a patient utilizing conventional orthodontic appliance with a stepped archwire to align teeth.

FIG. 15A illustrates a known brace installation where one tooth 700 at the upper right is recessed with respect to the surrounding teeth 701. In order to engage the selected tooth 700 properly, the archwire 702 is stepped up or down by way of bends 703 which are formed in the archwire 702 to meet the single slot 704 in a wire guide member 705. These bends 703 in the archwire 702 cannot be done with the flexible nitinol wires. Rather, they must be done with a stiff stainless steel wire which applies more force on all of the teeth, leading to patient discomfort. However, utilizing the structures of the embodiment of FIG. 14 of the present disclosure, there is no need for a step to be formed in the archwire 702. The multiple slots formed in the bracket permit the orthodontist to utilize memory-shape alloy archwires, such as nitinol without forming step bends therein, whereupon the steps would tend to disappear due to the heat of the patient's mouth returning the nitinol archwires back to their original configurations. The nitinol archwires may be placed in selected slots of the bracket in accordance with the manner in which the orthodontist seeks to apply pressure to selected teeth, thereby eliminating the need to use stiff stainless steel wire which may increase the discomfort of the patient.

Figure 13:
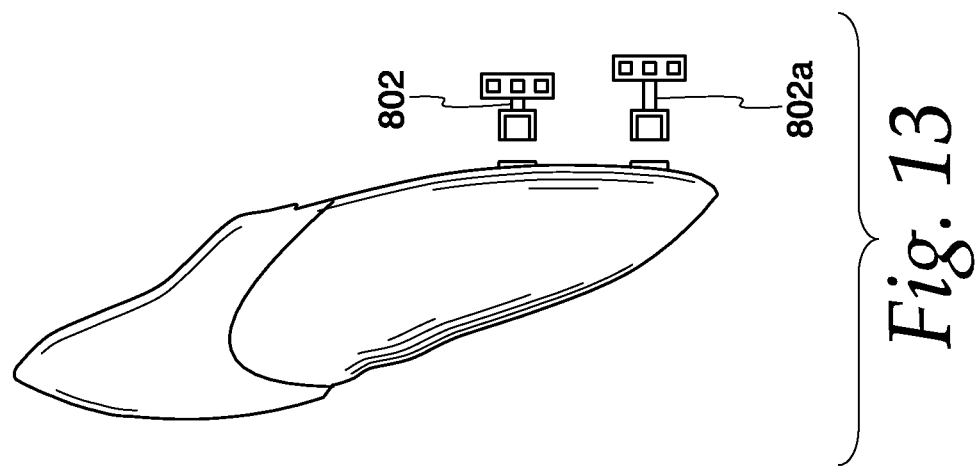
FIG. 13 is a diagrammatic (lateral) view of a tooth suitable for adjustment and two different magnetic guide members with posts of different lengths.
Figure 14F:
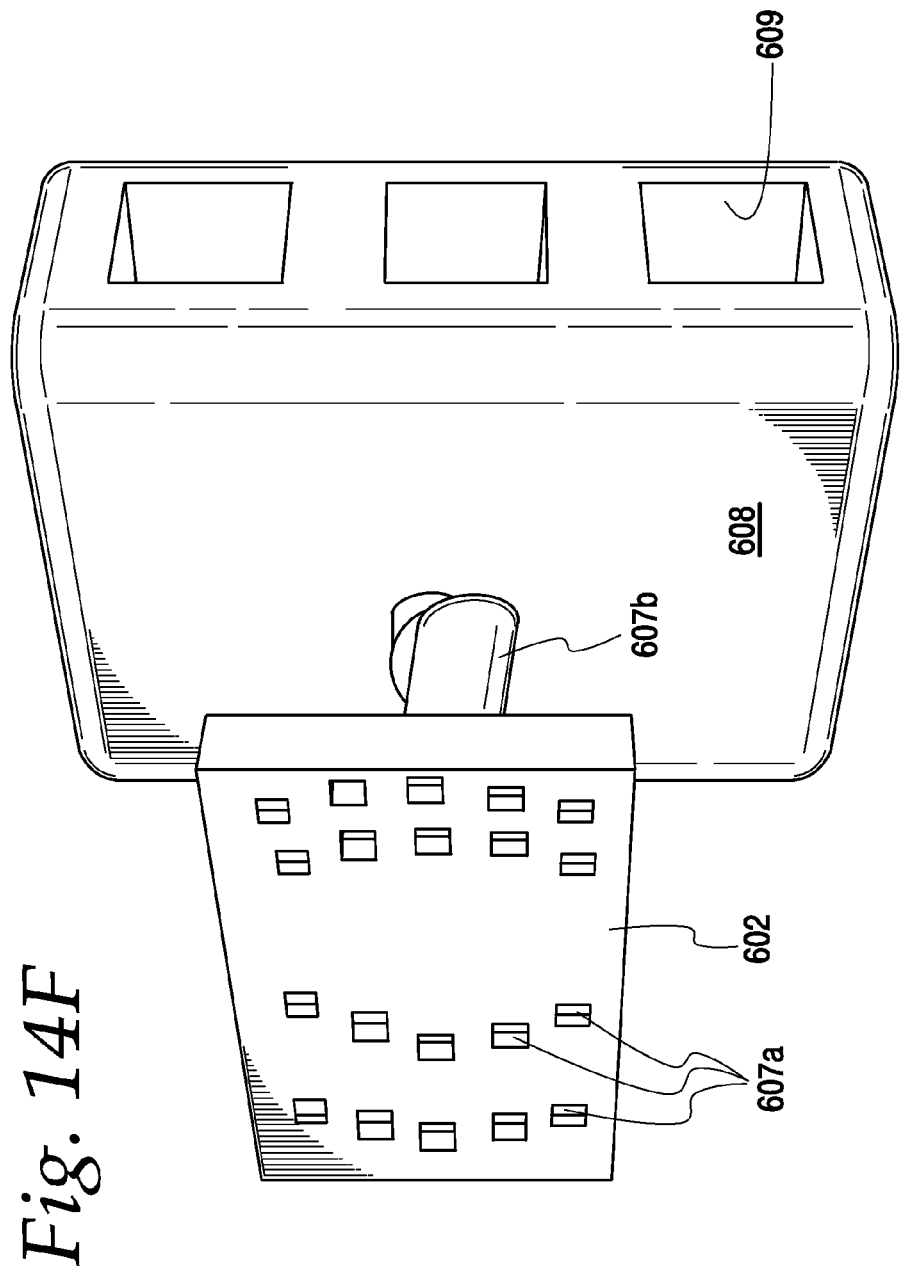
FIG. 14F is a rear perspective view of the arrangement of FIG. 14DE, illustrating the contact surface of the tooth mounting plate.

It can be seen from FIG. 13 that posts 802, 802a of different lengths may be used with wire guide members 800 that attach magnetically to selected teeth, or as shown in FIGS. 14-14F, the wire guide members 600 may have a mechanical means of attachment to the teeth and also utilize bendable posts (rods) 607, 607a, 607b of different lengths and different configurations to transfer forces to the teeth. Posts that have a curved configuration may also be used which will allow for placing step in or step out bends and torquing as that illustrated in FIG. 14D and FIG. 14F. The whole bracket system may also be manufactured as one unit where all adjustments can be made intraorally as illustrated in FIG. 14F.

Figure 15B:
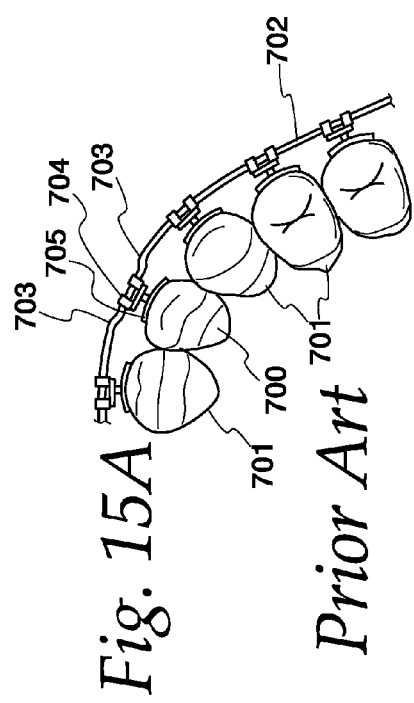
FIG. 15B is the same view as FIG. 15A, but with an orthodontic appliance of the present disclosure, illustrating the longer bracket for the one tooth archwire bracket.

As shown in FIG. 15B, which illustrates one advantage of the orthodontic appliances of the present disclosure, for use in imposing alignment upon teeth such as illustrated in FIG. 15A, the orthodontist can use a bracket assembly 800 that has a longer connecting post 802 than the posts 801 used in the other bracket assemblies 800 used in the appliance. In this regard, the systems of the present disclosure with utilize a flexible wire that follows a "natural" curve. As used herein, "natural" means following a contour of the teeth with no stepped bends formed in it between the ends of the archwires as at "C" in FIG. 15B. In other words, it contains no interruptions in the curve as are caused by the steps 703 in the archwire 702 in FIG. 15A. Instead, there is an uninterrupted arcuate path traced by the archwire 808. The magnet 804 in this embodiment will hold the wire guide 805 in place against the selected tooth 700, in contact with a metal plate 806 affixed to the selected tooth so that the curvature of the archwire 808 will transmit an alignment force through the magnet 804 and metal plate 806 to the tooth. The longer post 802 pushes the magnet 804 into contact with the metal plate 806 on the selected tooth a distance that maintains the archwire 808 at the natural curve so that the archwire 808 does not have to be bent in a stepped configuration as above. Hence, the present disclosure permits the use of nitinol wire, which otherwise would be too flexible to use.

Figure 15C:
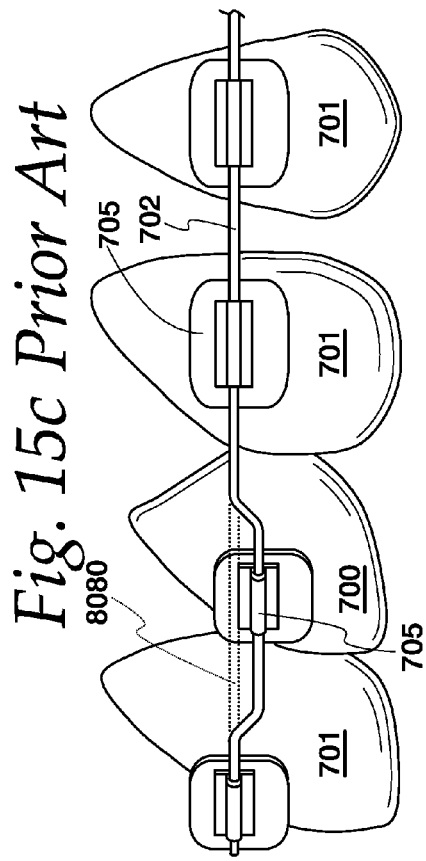
FIG. 15C is an enlarged front elevational view of a set of upper teeth secured together with an archwire having a step-down bend to bring one of the teeth downward within a patient's mouth; and, FIG. 16 is a side view of a tooth that needs torque movement and utilizing a support bracket with a bent, or curved, post attaching it to a magnet.

Another advantage of this embodiment lies in the presence of multiple slots 809 in the wire guides 805, as it also eliminates the need for stepped up or stepped down segments of the archwire 808, as illustrated in FIG. 15A. Such a prior art stepped down configuration of an archwire 702 is illustrated in FIG. 15C, which depicts a set of upper teeth 701 which are interconnected together by an archwire 702 that is received in wire guides 705 affixed to the teeth. One of the four teeth 701, namely tooth 700 needs to be brought down by the orthodontist to meet the desired biting line. In order to do so, a step-down bend 703 is formed in the archwire 702, which is further formed from a stiff stainless steel wire. In appliances of the present disclosure, the wire guide 805 is provided with a plurality of wire-receiving slots 809 that are preferably spaced apart from each other in the vertical direction. In an application such as that shown in FIG. 15C, but in accordance with the principles of the present disclosure, for bringing down a tooth, the metal plates 806 will be bonded to the teeth at the same relative elevation but one of the multiple wire-receiving slots 809 will be level with the wire curve (elevation), as shown by the dashed lines 8080 in FIG. 15C and the wire will be inserted into a slot above the elevation shown by the dashed lines 8080. In this manner, the nitinol wire will seek to return to its original curve, and it will exert a downward force on the tooth 700, thereby pulling it down without the use of a step-down bend. Likewise, the wire may be placed in a slot beneath the original curve 8080 and the archwire will tend to produce an upward force on that particular tooth.

Figure 16:
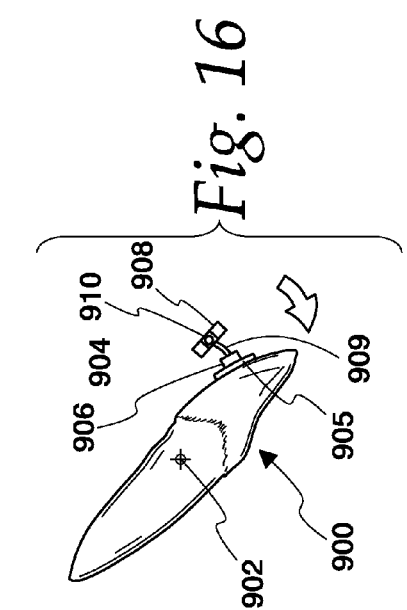

FIG. 16 illustrates a tooth 900 that is out of position and which needs torque applied to it on order to rotate it about a point of rotation. A bracket assembly 904 of the present disclosure is engaged with the tooth 900 by way of a metal engagement plate 905 affixed to the tooth 900. A magnet 906 of the bracket assembly 900 magnetically engages the plate 905 and a wire guide 908 is connected to the magnet 906 (or a housing therefor) by way of a post 909. In this instance, the post 909 is curved upwardly as illustrated and the archwire will exert torque forces on the tooth 900 of different magnitude and location depending on the particular slot in which it is contained. In this manner, there is no need to apply a step-down portion of an archwire 910 with a stiff stainless steel wire, as a more flexible nitonol wire 910 can be used. The longer posts 909 in this instance permit the orthodontist to maintain a curve with the archwire 910 without any stepped interruptions.

The appliances of the present disclosure may be easily installed in a patient. A patient will visit an orthodontist for an initial exam. The orthodontist will either take an impression or a digital scan of the patient's teeth. The final position of the teeth is determined processed into an STL file for printing by way of a 3-dimensional printer. With the help of corresponding software, extra room in designed into the aligner shell in order to accommodate the desired movement of the selected teeth. The aligner shell is further configured to provide seats, or pocket-like structures for holding the magnets or metal plates in place therewithin. A solid model of the selected teeth is then made to act as a positive for a mold that will define the final configuration of the hollow shell. The shell is then formed, such as by vacuum molding a resin sheet, such as EVA, over the mold positive.

In each aligner shell, a cavity is preferably defined for each specific tooth that requires movement and for other teeth that may serve as anchors for the hollow shell. Shells may be made that only have room for one tooth, such as the singular tooth caps described herein above. Or the shells may be made for a few selected teeth that need movement and as such may be formed to enclose a few teeth such as the four shown in FIG. 11B. Similarly, where multiple teeth in different locations within the mouth need to be aligned, the shells may extend for the entire set of upper or lower teeth between the rearmost molars of the mouth, as is shown in FIGS. 9 & 10. If all teeth need larger movement, movement of certain teeth may be accomplished sequentially by using a series of shells that are configured for stepped movement, i.e., shells with diminishing additional spaces as the selected teeth are moved fractional distances of the total movement distance.

The aligner shells may include have custom neodymium and other types of magnets and metal attachments for particular teeth movement. Most of the metal engagement plates will be attached to the lingual surfaces of teeth for better esthetics. If buccal movement of teeth is required, two repelling magnets may be positioned on the lingual side of a tooth and an opposing surface of the aligner shell, a metal engagement plate may be attached to the tooth and a magnet to the aligner shell on the buccal side thereof. Lingual movement of the tooth will have an opposite setup. Rotational movements will have the magnets spaced offset to, or at angles to the metal engagement plates.

While preferred embodiments have been shown and described, it is envisioned that those skilled in the art may devise various modifications without departing from the spirit and scope of the foregoing Description and the appended Claims.

What is claimed is:

1. An improved orthodontic appliance for aligning selected teeth of a wearer, comprising:
   a plurality of base plates adapted to be associated with respective selected teeth of the wearer;
   a plurality of wire guides for supporting an archwire in a curve between first and second locations on the teeth of the wearer, each of the wire guides including a slotted guide portion including a plurality of horizontal wire-receiving slots which are spaced vertically apart from each other, and a post extending between corresponding ones of the baseplates and wire guides; and,
   an archwire interconnecting said wire guides together in a continuous uninterrupted curve, the archwire engaging selected ones of the wire-receiving slots of each of said wire guides, and at least one of the posts having a length larger than other posts, whereby the longer post transfers a larger tooth moving force to its corresponding tooth than the other posts of the wire guides when said archwire is engaged with the wire guide having the longer post.

2. The orthodontic appliance of claim 1, wherein said archwire is a nitinol wire.

3. The orthodontic appliance of claim 1, wherein said wire-receiving slots are rectangular.

4. The orthodontic appliance of claim 1, wherein at least one of the posts has an angled configuration.

5. The orthodontic appliance of claim 1, wherein at least one post has a non-linear configuration.

6. The orthodontic appliance of claim 1, wherein said wire guides include first, second and third wire-receiving slots and the archwire engages different slots in different wire guides.

7. The orthodontic appliance of claim 1, wherein said posts are fixed to respective ones of the base plates.

8. The orthodontic appliance of claim 1, wherein said posts are fixed to housings and the housings magnetically engage said base plates.

9. The orthodontic appliance of claim 8, wherein the housings include magnetic inserts.

10. The orthodontic appliance of claim 8, wherein said housings engage said base plates of with a contact force of between about 50 and about 400 grams.

11. The orthodontic appliance of claim 1, wherein at least one of said posts is bent to apply a torque force on its corresponding tooth.

12. The orthodontic appliance of claim 1, wherein said archwire may be inserted into a first slot on a first wire-engaging member on a first tooth and into a second slot on a second wire-engaging member on a second tooth, adjacent to the first tooth, thereby eliminating the need for stepping said archwire.

13. The orthodontic appliance of claim 1, wherein some of said posts are curved and others of said posts are linear.

14. The orthodontic appliance of claim 1, wherein the posts are of varying lengths to avoid interruptions in said archwire uninterrupted continuous curve.

15. The orthodontic appliance of claim 1, wherein said base plates are affixed directly to corresponding teeth.

16. The orthodontic appliance of claim 1, wherein some of said base plates are affixed to selected, individual tooth caps, each such tooth cap including a hollow shell which receives a crown portion of its corresponding tooth.

17. The orthodontic appliance of claim 16, wherein at least one of the tooth cap hollow shells includes an ancillary cavity for engaging a retention lug affixed to a crown portion of the corresponding tooth.

* * * * *